United States Patent
Burgeson et al.

(12)

(10) Patent No.: US 7,125,666 B2
(45) Date of Patent: Oct. 24, 2006

(54) COLLAGEN XXII, A NOVEL HUMAN COLLAGEN AND USES THEREOF

(75) Inventors: Robert Eugene Burgeson, Palm Springs, CA (US); Manuel Koch, Cambridge, MA (US); Douglas R. Keene, Portland, OR (US); William Joseph Brunken, Canton, MA (US); Leena Bruckner-Tuderman, Munster (DE)

(73) Assignee: The General Hospital Corporation, Boston, MA (US)

( * ) Notice: Subject to any disclaimer, the term of this patent is extended or adjusted under 35 U.S.C. 154(b) by 300 days.

(21) Appl. No.: 10/202,167

(22) Filed: Jul. 24, 2002

(65) Prior Publication Data

US 2003/0143564 A1    Jul. 31, 2003

Related U.S. Application Data

(60) Provisional application No. 60/309,158, filed on Jul. 31, 2001.

(51) Int. Cl.
*C12Q 1/68* (2006.01)
*C12N 15/00* (2006.01)
*C12N 15/12* (2006.01)
*C12N 15/11* (2006.01)

(52) U.S. Cl. .................. 435/6; 435/320.1; 435/252.3; 435/325; 536/23.5; 536/23.1

(58) Field of Classification Search ............... 536/23.1, 536/23.5, 24.31, 24.3; 435/320.1, 325, 252.3, 435/6; 800/8, 14
See application file for complete search history.

(56) References Cited

U.S. PATENT DOCUMENTS

2003/0190715 A1 * 10/2003 Grosse et al. ............... 435/183

2004/0009474 A1 * 1/2004 Leach et al. .................... 435/6

FOREIGN PATENT DOCUMENTS

WO    WO 01/92523 A2 * 12/2001

OTHER PUBLICATIONS

Lee et al. "Biomedical applications of collagen", 2001,Int J Pharm, vol. 221(1-2):1-22.
Myllyharju et al., "Collagens and collagen-related diseases", 2001, Ann Med., vol. 33(1):7-21.
Database EST Accession No. BF196343, NCI-CGAP "7n68f06.x1 NCI_CGAP_Ov18 Homo sapiens cDNA clone," Nov. 2000, 4 pages.
Form PCT/ISA/220; "Notification of the International Search Report or the Declaration," as issued on Apr. 8, 2004, by the International Searching Authority, 6 pages.

* cited by examiner

*Primary Examiner*—James Martinell
(74) *Attorney, Agent, or Firm*—Fish & Richardson P.C.

(57) ABSTRACT

The invention provides isolated nucleic acids molecules, designated collagen XXII nucleic acid molecules, which encode a novel collagen. The invention also provides antisense nucleic acid molecules, recombinant expression vectors containing collagen XXII nucleic acid molecules, host cells into which the expression vectors have been introduced, and nonhuman transgenic animals in which a collagen XXII gene has been introduced or disrupted. The invention still further provides isolated collagen XXII proteins, fusion proteins, antigenic peptides and anti-collagen XXII antibodies. Diagnostic methods utilizing compositions of the invention are also provided.

32 Claims, 4 Drawing Sheets collagen XXII cDNA
GGGGCTGGCCCGAGGCTGCGGCGTTCTCCCCAAGGAAGTGTCTTCTCCGCTTTCCCTGTTCTTCT
GTTTCTCACACACTTTCTATCTCATTCTGTAACTTTCAAGCCTTTCCTTCTAACTGTATGTATTT
AGTTACTTGTTTTCAAGCTGGTTCCCTCTCTGGCCCCCTGGCCTGGGGAAAGCCTCCACACTTAC
TGCGGGTCTTGTTTAGAGTCTGAGTTTGTGAGATTATTTGGGGCAGAGTGGGCGAGTGGCTGACA
GGTGACCCCCAGGAGGAGGATTCCTGGGGCTGGTGTCTTCTCCCAGCTGCTGCTTCCAGTGGGCC
TGGGCCCAGGACTGGACCTCCGCTGGCACCCCTGAGTGCCTCCCTGCCAGGCCATGCTGCTGTAG
ACCCTAACAGCGTCTCTTCCTGGCCAAGAGAAGCCTGTCCCCAAGAACAGGAGAGCC<u>ATG</u>GCCGG
CCTCCGAGGGAACGCTGTGGCTGGCCTCCTCTGGATGCTGCTGCTGTGGAGTGGGGCGGCGGCT
GCCAGGCTCAGCGGGCAGGTTGCAAAAGTGTCCACTACGATCTGGTCTTCCTCCTGGACACCTCC
TCCAGCGTGGGCAAGGAGGACTTTGAGAAGGTCCGGCAGTGGGTGGCCAACCTGGTGGACACCTT
CGAGGTGGGCCCCGACCGCACCCGTGTGGGGGTCGTGCGCTACAGCGACCGGCCCACCACGGCCT
TCGAGTTGGGACTCTTTGGCTCGCAGGAGGAGGTCAAGGCGGCTGCCCGGCGTCTCGCCTACCAC
GGGGGCAACACCAACACGGGAGACGCGCTCCGCTACATCACGGCCCGCAGCTTCTCCCCACACGC
CGGCGGCCGCCCCAGGGACCGCGCCTACAAGCAGGTGGCCATCCTGCTCACCGACGGCCGCAGCC.
AGGACCTGGTGCTGGACGCCGCGGCGGCAGCCCACCGCGCTGGCATCCGCATCTTTGCCGTGGGC
GTGGGCGAGGCACTCAAGGAGGAGCTGGAGGAGATCGCCTCAGAGCCCAAGTCCGCCCACGTCTT
CCACGTGTCCGACTTCAATGCCATCGACAAGATCCGGGGCAAGCTGCGGCGCCGTCTTTGTGAAA
ATGTGCTCTGTCCTAGCGTTCGTGTAGAAGGAGATCGCTTTAAGCACACCAATGGAGGAACCAAG
GAAATCACAGGTTTTGACCTGATGGATTTGTTCAGTGTGAAGGAAATCTTGGGGAAGAGAGAGAA
TGGAGCTCAGAGTTCCTATGTACGGATGGGATCCTTCCCTGTGGTGCAAAGTACTGAGGATGTGT
TCCCCCAAGGTTTACCTGATGAGTACGCCTTTGTCACAACCTTCCGGTTCAGGAAAACCTCTCGG
AAGGAAGACTGGTATATCTGGCAGGTCATCGACCAGTACGGCATCCCACAGGTCTCCATCCGGCT
GGATGGTGAAAACAAGGCAGTCGAGTACAACGCTGTGGGTGCCATGAAAGATGCTGTCAGGGTGG
TCTTCCGAGGTTCTCGGGTCAATGACCTCTTTGACCGGGACTGGCACAAGATGGCCCTGAGCATC
CAGGCCCAGAACGTCTCCCTGCACATTGACTGTGCGCTGGTGCAGACACTACCCATCGAGGAACG
GGAGAACATTGACATCCAGGGCAAGACTGTGATTGGCAAGCGCCTCTACGACAGTGTGCCCATTG
ACTTTGACCTACAGCGGATTGTGATCTATTGTGACTCGAGACACGCAGAATTGGAGACTTGTTGT
GATATCCCCTCGGGTCCGTGCCAGGTGACCGTGGTGACAGAGCCTCCACCTCCACCCCCACCCCA
GCGGCCTCCCACCCCAGGCAGTGAACAGATTGGGTTTTTGAAGACCATCAACTGCTCCTGCCCAG
CTGGAGAGAAGGGTGAAATGGGAGTTGCTGGCCCCATGGGGCTCCCTGGTCCAAAGGGAGACATA
GGAGCCATTGGGCCGGTTGGCGCTCCTGGACCTAAGGGAGAGAAAGGTGATGTGGGCATAGGACC
TTTTGGCCAAGGGGAAAAGGGTGAAAAGGGTTCCCTGGGCCTGCCCGGCCCCCTGGGAGAGACG
GCAGCAAAGGCATGAGAGGGGAGCCAGGAGAGCTGGGAGAGCCGGGGCTGCCGGGTGAGGTCGGC

FIGURE 1A

```
ATGCGGGGGCCCCAAGGACCACCTGGACTCCCCGGACCTCCTGGACGTGTCGGAGCTCCTGGTCT
CCAAGGAGAACGAGGTGAAAAGGGAACTCGAGGAGAAAAGGGAGAGCGAGGCCTGGATGGATTCC
CTGGGAAGCCTGGGGACACAGGACAGCAGGGCAGGCCCGGCCCTTCTGGTGTGGCAGGACCCCAG
GGAGAAAAGGGTGACGTGGGACCTGCGGGGCCACCTGGTGTACCAGGCTCAGTGGTGCAGCAAGA
GGGCTTGAAAGGGGAACAGGGAGCTCCAGGACCCAGAGGTCACCAAGGCGCCCCGGTCCTCCAG
GAGCTCGGGGTCCAATAGGCCCAGAAGGCAGGGATGGACCTCCTGGTTTGCAAGGTCTCCGAGGG
AAGAAAGGTGACATGGGACCACCTGGAATCCCTGGATTGCTGGGCTGCAGGGCCCTCCAGGACC
CCCTGGTGTCCCAGGCCCCCTGGACCGGGAGGTTCTCCGGGTTTGCCTGGAGAGATCGGCTTCC
CGGGAAGCCTGGACCTCCTGGGCCCACGGGACCCCTGGAAAGGACGGGCCAAATGGACCACCA
GGTCCGCCAGGAACCAAGGGAGAACCAGGAGAAGAGGGGAAGATGGTCTGCCTGGAAAACCAGG
CCTTCGGGGAGAAATTGGGGAGCAGGGCCTGGCAGGCCGACCTGGAGAGAAGGGAGAAGCAGGCC
TCCCAGGGGCTCCAGGCTTCCAGGTGTGAGAGGAGAGAAAGGAGACCAGGGAGAAAAGGTGAA
CTGGGACTTCCAGGACTGAAAGGTGACCGAGGTGAAAAGGGTGAAGCTGGTCCTGCAGGCCCTCC
CGGGTTACCTGGAACTACATCCCTGTTCACACCACATCCACGGATGCCCGGAGAACAAGGGCCCA
AAGGAGAGAAGGGCGATCCAGGCCTGCCTGGGGAACCGGGACTGCAGGGCCGTCCTGGAGAATTG
GGGCCTCAGGGACCCACTGGACCACCGGGTGCCAAGGGACAGGAAGGTGCACATGGGGCTCCTGG
AGCAGCTGGAAACCCCGGTGCTCCCGGACATGTCGGTGCCCCGGTCCCAGTGGCCCTCCAGGAA
GTGTGGGTGCTCCCGGCCTCAGAGGCACCCCAGGGAAAGATGGGGAGCGTGGTGAGAAGGGTGCA
GCGGGGGAAGAAGGCAGCCCAGGGCCAGTTGGTCCCAGGGGAGATCCTGGTGCTCCTGGGCTCCC
TGGGCCGCCCGGAAAAGGGAAGGATGGAGAGCCGGGACTCCGTGGATCACCTGGACTCCCTGGAC
CCCTAGGAACCAaggctgcttgcggaaaagtcagagggtcagaaaactgtgcactgggagggcaa
tgtgttaAGGGGGATCGAGGAGCTCCTGGGATCCCTGGTTCTCCTGGCAGCCGTGGTGACCCAGG
CATTGGGGTTGCTGGCCCTCCTGGCCCTTCCGGACCACCAGGAGACAAAGGATCCCCGGGATCAC
GAGGCTTACCTGGATTCCCTGGCCCCAGGGCCCAGCCGGCCGGGACGGTGCACCAGGAAATCCA
GGAGAAGAGGGCCTCCTGGCAAGCCGGGCCTCTCTTCACTACTGTCTCCAGGGGACATAAATCT
CTTGGCTAAGGATGTGTGCAATGACTGCCCTCCTGGCCCCCAGGCCTCCCTGGTCTACCAGGTT
TTAAAGGGGACAAAGGTGTCCCAGGAAAGCCAGGGAGAGAAGGCACAGAAGGGAAAAAGGGAGAG
GCTGGGCCTCCAGGCCTACCAGGGCCCCCAGGAATAGCTGGACCACAGGGAAGTCAAGGAGAACG
TGGTGCAGATGGTGAGGTTGGGCAGAAAGGTGATCAGGGTCATCCTGGAGTTCCAGGTTTCATGG
GGCCCCAGGGAACCCCGGGCCACCAGGGGCAGATGGAATTGCAGGAGCTGCTGGACCACCAGGA
ATCCAAGGGTCACCTGGGAAAGAAGGCCCTCCTGGCCCCAAGGCCCATCTGGATTACCCGGAAT
CCCAGGAGAAGAAGGCAAAGAGGGCAGAGATGGAAAGCCGGGTCCCCCTGGAGAGCCGGGCAAAG
CAGGAGAGCCAGGTCTACCAGGACCAGAGGGTGCCCGAGGCCCACCTGGCTTCAAGGGACACACA
GGCGATTCTGGTGCACCCGGTCCCCGGGGAGAGTCTGGTGCCATGGGGCTTCCTGGTCAGGAAGG
GTTACCAGGAAAAGATGGTGACACTGGACCCACTGGGCCACAGGGTCCCCAAGGACCAAGGGGCC
```

FIGURE 1B

```
CACCGGGCAAGAATGGATCACCGGGATCTCCAGGAGAGCCTGGCCCTTCAGGAACCCCTGGCCAG
AAAGGAAGCAAAGGGGAAAATGGCAGCCCAGGACTTCCTGGCTTCCTGGGTCCCCGTGGGCCTCC
GGGAGAACCAGGAGAGAAAGGAGTCCCAGGCAAGGAGGGGGTCCCTGGGAAGCCTGGAGAGCCTG
GATTCAAAGGAGAAAGGGGAGATCCTGGGATCAAAGGTGACAAAGGACCTCCTGGTGGAAAAGGC
CAGCCTGGGGACCCTGGAATCCCAGGCCACAAAGGCCACACAGGCCTGATGGGTCCCCAAGGACT
ACCTGGGGAGAATGGACCAGTTGGACCCCAGGGCCTCCAGGCCAGCCGGGATTTCCAGGACTGA
GGGGGGAGTCTCCATCCATGGAAACCCTGCGTCGGCTTATTCAAGAAGAGCTGGGGAAGCAGCTT
GAAACCAGACTCGCCTACCTCCTGGCCCAGATGCCCCGGCGTACATGAAGTCATCTCAAGGCAG
ACCTGGGCCCCAGGGCCCCTGGAAAGATGGGCTTCCAGGCCGGGCCGGCCCCATGGGGGAGC
CAGGTCGTCCTGGGCAGGGGGTCTGGAAGGACCCTCTGGACCCATAGGTCCCAAAGGTGAGCGA
GGAGCCAAAGGTGACCCAGGTGCACCTGGAGTTGGCCTCCGAGGCGAGATGGGACCCCCTGGAAT
CCCAGGTCAACCCGGGGAACCTGGCTATGCTAAAGATGGACTTCCTGGGATCCCTGGCCCTCAAG
GGGAGACAGGACCAGCTGGACATCCTGGCCTCCCAGGACCTCCCGGTCCCCAGGCCAATGTGAC
CCTTCCCAGTGTGCCTACTTCGCCAGCCTTGCTGCCCGGCCGGGTAATGTGAAGGGTCCCTAAAG
GACTCTGGAAAGCCAGAAGACTGCAGTGGATTTCTGAAACTTGAACTCAGAGCCCAGTGGGAAGC
CAGAGGTCTTGAAAGACTTCAGCCATGTGTTCCTTTTTTTTTCTTTCTTTTATCGTTTGCTTTT
TGTTTTATTTTCTTGAGAGACCTCAAAATTATTAAATCCAACAGACGCTGCCGGTCGGTCAGATT
ATTATTAATATTATTGTTGTTGTTAATTATTATTATTATTTCATATGCTGATGCTTTGTGAGTTC
TTTTCCACTCCTTTAAAGTTGGGAAAACTTGATTCGTGGGGCAGGAGATTGTTTCTTCATTCTTC
TGACAGCCCCCATCTGACGCGTAACTGCCCATTTTAAGGAAACTCTTGGTGCTACAAAACCCTGA
CCAGACACTTGGCAAATTTACCTCTTTCTTCAAAAGAAAAACTTTAAGAAAATGAGCCAATGGGC
TTCATTCTCAGTCATGCCCGGAGATCACCCAGGAGAAATAATACAAACACCACCACTGTCCAGAG
AGAGTAAAGAAGCAGAAAGAGAAAGAATTTGCAACCATGAGGAATGTTCCCACCTCCCGACGGGA
CGTGCATTTGGAAAACACAGAATCAGCCCTCAGGGTGCACTCCAGCCACCTCAGTGCTCTAAGCT
CACAGAAGTGAAATAATGTCTGTGGGTTGGCAATGGCTTTGTGGGATCATATGTCTTGGCCAAAG
ATGGGAAAACCTATGTTGAAGAGGCAGCCCTTGAGTGTTAATTTGTCTTCTAAACTGTGTAAGGC
CCCTTCAAGTTCCTCTTGTTGGTTTCAATTATATTAATTATAAACAAGTGGATGTGGTGACCAT
CCACTTGTGTTTCCCTAATGATGGGCAGTTGGCCAGGGCACTGACCAGAGCTGGGAAATTTGTAT
CTCCAAGGCGGCTCTGTCTCTGAAATAAATGGCATCAAGTGCATGTGTGTATGCGACATGCCCTG
CCTGAACAGGTGCTCAATAAATCCAAGTTTCCTTCTCTTGAAAAAAA
```

FIGURE 1C

Collagen 22 amino acid sequence

MAGLRGNAVAGLLWMLLLWSGGGGCQAQRAGCKSVHYDLVFLLDTSSSVGKEDFEKVRQW 60
VANLVDTFEVGPDRTRVGVVRYSDRPTTAFELGLFGSQEEVKAAARRLAYHGGNTNTGDA 120
LRYITARSFSPHAGGRPRDRAYKQVAILLTDGRSQDLVLDAAAAAHRAGIRIFAVGVGEA 180
LKEELEEIASEPKSAHVFHVSDFNAIDKIRGKLRRRLCENVLCPSVRVEGDRFKHTNGGT 240
KEITGFDLMDLFSVKEILGKRENGAQSSYVRMGSFPVVQSTEDVFPQGLPDEYAFVTTFR 300
FRKTSRKEDWYIWQVIDQYGIPQVSIRLDGENKAVEYNAVGAMKDAVRVVFRGSRVNDLF 360
DRDWHKMALSIQAQNVSLHIDCALVQTLPIEERENIDIQGKTVIGKRLYDSVPIDFDLQR 420
IVIYCDSRHAELETCCDIPSGPCQVTVVTEPPPPPPPQRPPTPGSEQIGFLLKINCSCPA 480
GEKGEMGVAGPMGLPGPKGDIGAIGPVGAPGPKGEKGDVGIGPFGQGEKGEKGSLGLPGP 540
PGRDGSKGMRGEPGELGEPGLPGEVGMRGPQGPPGLPGPPGRVGAPGLQGERGEKGTRGE 600
KGERGLDGFPGKPGDTGQQGRPGPSGVAGPQGEKGDVGPAGPPGVPGSVVQQEGLKGEQG 660
APGPRGHQGAPGPPGARGPIGPEGRDGPPGLQGLRGKKGDMGPPGIPGLLGLQGPPGPPG 720
VPGPPGPGGSPGLPGEIGFPGKPGPPGPTGPPGKDGPNGPPGPPGTKGEPGERGEDGLPG 780
KPGLRGEIGEQGLAGRPGEKGEAGLPGAPGFPGVRGEKGDQGEKGELGLPGLKGDRGEKG 840
EAGPAGPPGLPGTTSLFTPHPRMPGEQGPKGEKGDPGLPGEPGLQGRPGELGPQGPTGPP 900
GAKGQEGAHGAPGAAGNPGAPGHVGAPGPSGPPGSVGAPGLRGTPGKDGERGEKGAAGEE 960
GSPGPVGPRGDPGAPGLPGPPGKGKDGEPGLRGSPGLPGPLGTKAACGKVRGSENCALGG 1020
QCVKGDRGAPGIPGSPGSRGDPGIGVAGPPGPSGPPGDKGSPGSRGLPGFPGPQGPAGRD 1080
GAPGNPGERGPPGKPGLSSLLSPGDINLLAKDVCNDCPPGPPGLPGLPGFKGDKGVPGKP 1140
GREGTEGKKGEAGPPGLPGPPGIAGPQGSQGERGADGEVGQKGDQGHPGVPGFMGPPGNP 1200
GPPGADGIAGAAGPPGIQGSPGKEGPPGPQGPSGLPGIPGEEGKEGRDGKPGPPGEPGKA 1260
GEPGLPGPEGARGPPGFKGHTGDSGAPGPRGESGAMGLPGQEGLPGKDGDTGPTGPQGPQ 1320
GPRGPPGKNGSPGSPGEPGPSGTPGQKGSKGENGSPGLPGFLGPRGPPGEPGEKGVPGKE 1380
GVPGKPGEPGFKGERGDPGIKGDKGPPGGKGQPGDPGIPGHKGHTGLMGPQGLPGENGPV 1440
GPPGPPGQPGFPGLRGESPSMETLRRLIQEELGKQLETRLAYLLAQMPPAYMKSSQGRPG 1500
PPGPPGKDGLPGRAGPMGEPGRPGQGGLEGPSGPIGPKGERGAKGDPGAPGVGLRGEMGP 1560
PGIPGQPGEPGYAKDGLPGIPGPQGETGPAGHPGLPGPPGPPGQCDPSQCAYFASLAARP 1620
GNVKGP*

FIGURE 2

SEQUENCE LISTING

<160> NUMBER OF SEQ ID NOS: 3

<210> SEQ ID NO 1
<211> LENGTH: 6352
<212> TYPE: DNA
<213> ORGANISM: Homo sapiens
<220> FEATURE:
<221> NAME/KEY: CDS
<222> LOCATION: (448)...(5325)

<400> SEQUENCE: 1

```
ggggctggcc cgaggctgcg gcgttctccc caaggaagtg tcttctccgc tttccctgtt      60
cttctgtttc tcacacactt tctatctcat tctgtaactt tcaagccttt ccttctaact     120
gtatgtattt agttacttgt tttcaagctg gttccctctc tggcccctg gcctggggaa     180 agcctccaca cttactgcgg gtcttgttta gagtctgagt ttgtgagatt atttggggca     240
gagtgggcga gtggctgaca ggtgacccc aggaggagga ttcctggggc tggtgtcttc     300
tcccagctgc tgcttccagt gggcctgggc ccaggactgg acctccgctg gcaccctga     360 gtgcctccct gccaggccat gctgctgtag accctaacag cgtctcttcc tggccaagag     420
aagcctgtcc ccaagaacag gagagcc atg gcc ggc ctc cga ggg aac gct gtg     474
                                 Met Ala Gly Leu Arg Gly Asn Ala Val
                                   1               5 gct ggc ctc ctc tgg atg ctg ctg ctg tgg agt ggg ggc ggc ggc tgc         522
Ala Gly Leu Leu Trp Met Leu Leu Leu Trp Ser Gly Gly Gly Gly Cys
 10              15                  20                  25 cag gct cag cgg gca ggt tgc aaa agt gtc cac tac gat ctg gtc ttc         570
Gln Ala Gln Arg Ala Gly Cys Lys Ser Val His Tyr Asp Leu Val Phe
             30                  35                  40 ctc ctg gac acc tcc tcc agc gtg ggc aag gag gac ttt gag aag gtc         618
Leu Leu Asp Thr Ser Ser Ser Val Gly Lys Glu Asp Phe Glu Lys Val
         45                  50                  55 cgg cag tgg gtg gcc aac ctg gtg gac acc ttc gag gtg ggc ccc gac         666
Arg Gln Trp Val Ala Asn Leu Val Asp Thr Phe Glu Val Gly Pro Asp
     60                  65                  70 cgc acc cgt gtg ggg gtc gtg cgc tac agc gac cgg ccc acc acg gcc         714
Arg Thr Arg Val Gly Val Val Arg Tyr Ser Asp Arg Pro Thr Thr Ala
 75                  80                  85 ttc gag ttg gga ctc ttt ggc tcg cag gag gag gtc aag gcg gct gcc         762
Phe Glu Leu Gly Leu Phe Gly Ser Gln Glu Glu Val Lys Ala Ala Ala
 90                  95                 100                 105 cgg cgt ctc gcc tac cac ggg ggc aac acc aac acg gga gac gcg ctc         810
Arg Arg Leu Ala Tyr His Gly Gly Asn Thr Asn Thr Gly Asp Ala Leu
             110                 115                 120 cgc tac atc acg gcc cgc agc ttc tcc cca cac gcc ggc ggc cgc ccc         858
```

```
                Arg Tyr Ile Thr Ala Arg Ser Phe Ser Pro His Ala Gly Gly Arg Pro
                                125             130             135 agg gac cgc gcc tac aag cag gtg gcc atc ctg ctc acc gac ggc cgc      906
Arg Asp Arg Ala Tyr Lys Gln Val Ala Ile Leu Leu Thr Asp Gly Arg
        140             145             150 agc cag gac ctg gtg ctg gac gcc gcg gcg gca gcc cac cgc gct ggc      954
Ser Gln Asp Leu Val Leu Asp Ala Ala Ala Ala Ala His Arg Ala Gly
    155             160             165 atc cgc atc ttt gcc gtg ggc gtg ggc gag gca ctc aag gag gag ctg     1002
Ile Arg Ile Phe Ala Val Gly Val Gly Glu Ala Leu Lys Glu Glu Leu
170             175             180             185 gag gag atc gcc tca gag ccc aag tcc gcc cac gtc ttc cac gtg tcc     1050
Glu Glu Ile Ala Ser Glu Pro Lys Ser Ala His Val Phe His Val Ser
                190             195             200 gac ttc aat gcc atc gac aag atc cgg ggc aag ctg cgg cgc cgt ctt     1098
Asp Phe Asn Ala Ile Asp Lys Ile Arg Gly Lys Leu Arg Arg Arg Leu
            205             210             215 tgt gaa aat gtg ctc tgt cct agc gtt cgt gta gaa gga gat cgc ttt     1146
Cys Glu Asn Val Leu Cys Pro Ser Val Arg Val Glu Gly Asp Arg Phe
        220             225             230 aag cac acc aat gga gga acc aag gaa atc aca ggt ttt gac ctg atg     1194
Lys His Thr Asn Gly Gly Thr Lys Glu Ile Thr Gly Phe Asp Leu Met
    235             240             245 gat ttg ttc agt gtg aag gaa atc ttg ggg aag aga gag aat gga gct     1242
Asp Leu Phe Ser Val Lys Glu Ile Leu Gly Lys Arg Glu Asn Gly Ala
250             255             260             265 cag agt tcc tat gta cgg atg gga tcc ttc cct gtg gtg caa agt act     1290
Gln Ser Ser Tyr Val Arg Met Gly Ser Phe Pro Val Val Gln Ser Thr
                270             275             280 gag gat gtg ttc ccc caa ggt tta cct gat gag tac gcc ttt gtc aca     1338
Glu Asp Val Phe Pro Gln Gly Leu Pro Asp Glu Tyr Ala Phe Val Thr
            285             290             295 acc ttc cgg ttc agg aaa acc tct cgg aag gaa gac tgg tat atc tgg     1386
Thr Phe Arg Phe Arg Lys Thr Ser Arg Lys Glu Asp Trp Tyr Ile Trp
        300             305             310 cag gtc atc gac cag tac ggc atc cca cag gtc tcc atc cgg ctg gat     1434
Gln Val Ile Asp Gln Tyr Gly Ile Pro Gln Val Ser Ile Arg Leu Asp
    315             320             325 ggt gaa aac aag gca gtc gag tac aac gct gtg ggt gcc atg aaa gat     1482
Gly Glu Asn Lys Ala Val Glu Tyr Asn Ala Val Gly Ala Met Lys Asp
330             335             340             345 gct gtc agg gtg gtc ttc cga ggt tct cgg gtc aat gac ctc ttt gac     1530
Ala Val Arg Val Val Phe Arg Gly Ser Arg Val Asn Asp Leu Phe Asp
                350             355             360 cgg gac tgg cac aag atg gcc ctg agc atc cag gcc cag aac gtc tcc     1578
Arg Asp Trp His Lys Met Ala Leu Ser Ile Gln Ala Gln Asn Val Ser
            365             370             375 ctg cac att gac tgt gcg ctg gtg cag aca cta ccc atc gag gaa cgg     1626
Leu His Ile Asp Cys Ala Leu Val Gln Thr Leu Pro Ile Glu Glu Arg
        380             385             390 gag aac att gac atc cag ggc aag act gtg att ggc aag cgc ctc tac     1674
Glu Asn Ile Asp Ile Gln Gly Lys Thr Val Ile Gly Lys Arg Leu Tyr
    395             400             405 gac agt gtg ccc att gac ttt gac cta cag cgg att gtg atc tat tgt     1722
Asp Ser Val Pro Ile Asp Phe Asp Leu Gln Arg Ile Val Ile Tyr Cys
410             415             420             425 gac tcg aga cac gca gaa ttg gag act tgt tgt gat atc ccc tcg ggt     1770
Asp Ser Arg His Ala Glu Leu Glu Thr Cys Cys Asp Ile Pro Ser Gly
                430             435             440
```

-continued

| | |
|---|---|
| ccg tgc cag gtg acc gtg gtg aca gag cct cca cct cca ccc cca ccc<br>Pro Cys Gln Val Thr Val Val Thr Glu Pro Pro Pro Pro Pro Pro Pro<br>445                       450                       455 | 1818 |
| cag cgg cct ccc acc cca ggc agt gaa cag att ggg ttt ttg aag acc<br>Gln Arg Pro Pro Thr Pro Gly Ser Glu Gln Ile Gly Phe Leu Lys Thr<br>    460                      465                       470 | 1866 |
| atc aac tgc tcc tgc cca gct gga gag aag ggt gaa atg gga gtt gct<br>Ile Asn Cys Ser Cys Pro Ala Gly Glu Lys Gly Glu Met Gly Val Ala<br>475                       480                       485 | 1914 |
| ggc ccc atg ggg ctc cct ggt cca aag gga gac ata gga gcc att ggg<br>Gly Pro Met Gly Leu Pro Gly Pro Lys Gly Asp Ile Gly Ala Ile Gly<br>490                  495                 500                 505 | 1962 |
| ccg gtt ggc gct cct gga cct aag gga gag aaa ggt gat gtg ggc ata<br>Pro Val Gly Ala Pro Gly Pro Lys Gly Glu Lys Gly Asp Val Gly Ile<br>                 510                 515                 520 | 2010 |
| gga cct ttt ggc caa ggg gaa aag ggt gaa aag ggt tcc ctg ggc ctg<br>Gly Pro Phe Gly Gln Gly Glu Lys Gly Glu Lys Gly Ser Leu Gly Leu<br>           525                     530                   535 | 2058 |
| ccc ggc ccc cct ggg aga gac ggc agc aaa ggc atg aga ggg gag cca<br>Pro Gly Pro Pro Gly Arg Asp Gly Ser Lys Gly Met Arg Gly Glu Pro<br>    540                      545                       550 | 2106 |
| gga gag ctg gga gag ccg ggg ctg ccg ggt gag gtc ggc atg cgg ggg<br>Gly Glu Leu Gly Glu Pro Gly Leu Pro Gly Glu Val Gly Met Arg Gly<br>555                       560                     565 | 2154 |
| ccc caa gga cca cct gga ctc ccc gga cct cct gga cgt gtc gga gct<br>Pro Gln Gly Pro Pro Gly Leu Pro Gly Pro Pro Gly Arg Val Gly Ala<br>570                       575                 580                 585 | 2202 |
| cct ggt ctc caa gga gaa cga ggt gaa aag gga act cga gga gaa aag<br>Pro Gly Leu Gln Gly Glu Arg Gly Glu Lys Gly Thr Arg Gly Glu Lys<br>                 590                 595                 600 | 2250 |
| gga gag cga ggc ctg gat gga ttc cct ggg aag cct ggg gac aca gga<br>Gly Glu Arg Gly Leu Asp Gly Phe Pro Gly Lys Pro Gly Asp Thr Gly<br>605                       610                     615 | 2298 |
| cag cag ggc agg ccc ggc cct tct ggt gtg gca gga ccc cag gga gaa<br>Gln Gln Gly Arg Pro Gly Pro Ser Gly Val Ala Gly Pro Gln Gly Glu<br>    620                      625                       630 | 2346 |
| aag ggt gac gtg gga cct gcg ggg cca cct ggt gta cca ggc tca gtg<br>Lys Gly Asp Val Gly Pro Ala Gly Pro Pro Gly Val Pro Gly Ser Val<br>635                       640                       645 | 2394 |
| gtg cag caa gag ggc ttg aaa ggg gaa cag gga gct cca gga ccc aga<br>Val Gln Gln Glu Gly Leu Lys Gly Glu Gln Gly Ala Pro Gly Pro Arg<br>650                       655                 660                 665 | 2442 |
| ggt cac caa ggc gcc ccc ggt cct cca gga gct cgg ggt cca ata ggc<br>Gly His Gln Gly Ala Pro Gly Pro Pro Gly Ala Arg Gly Pro Ile Gly<br>                 670                 675                 680 | 2490 |
| cca gaa ggc agg gat gga cct cct ggt ttg caa ggt ctc cga ggg aag<br>Pro Glu Gly Arg Asp Gly Pro Pro Gly Leu Gln Gly Leu Arg Gly Lys<br>                 685                 690                 695 | 2538 |
| aaa ggt gac atg gga cca cct gga atc cct gga ttg ctg ggg ctg cag<br>Lys Gly Asp Met Gly Pro Pro Gly Ile Pro Gly Leu Leu Gly Leu Gln<br>700                       705                     710 | 2586 |
| ggc cct cca gga ccc cct ggt gtc cca ggc ccc cct gga ccg gga ggt<br>Gly Pro Pro Gly Pro Pro Gly Val Pro Gly Pro Pro Gly Pro Gly Gly<br>715                       720                     725 | 2634 |
| tct ccg ggt ttg cct gga gag atc ggc ttc ccg gga aag cct gga cct<br>Ser Pro Gly Leu Pro Gly Glu Ile Gly Phe Pro Gly Lys Pro Gly Pro<br>730                       735                 740                 745 | 2682 |
| cct ggg ccc acg gga ccc cct gga aag gac ggg cca aat gga cca cca<br>Pro Gly Pro Thr Gly Pro Pro Gly Lys Asp Gly Pro Asn Gly Pro Pro<br>                 750                 755                 760 | 2730 |

-continued

| | |
|---|---|
| ggt ccg cca gga acc aag gga gaa cca gga gaa aga ggg gaa gat ggt<br>Gly Pro Pro Gly Thr Lys Gly Glu Pro Gly Glu Arg Gly Glu Asp Gly<br>     765                           770                        775 | 2778 |
| ctg cct gga aaa cca ggc ctt cgg gga gaa att ggg gag cag ggc ctg<br>Leu Pro Gly Lys Pro Gly Leu Arg Gly Glu Ile Gly Glu Gln Gly Leu<br>780                          785                        790 | 2826 |
| gca ggc cga cct gga gag aag gga gaa gca ggc ctc cca ggg gct cca<br>Ala Gly Arg Pro Gly Glu Lys Gly Glu Ala Gly Leu Pro Gly Ala Pro<br>795                          800                        805 | 2874 |
| ggc ttc cca ggt gtg aga gga gag aaa gga gac cag gga gaa aaa ggt<br>Gly Phe Pro Gly Val Arg Gly Glu Lys Gly Asp Gln Gly Glu Lys Gly<br>810                          815                        820                        825 | 2922 |
| gaa ctg gga ctt cca gga ctg aaa ggt gac cga ggt gaa aag ggt gaa<br>Glu Leu Gly Leu Pro Gly Leu Lys Gly Asp Arg Gly Glu Lys Gly Glu<br>                          830                        835                        840 | 2970 |
| gct ggt cct gca ggc cct ccc ggg tta cct gga act aca tcc ctg ttc<br>Ala Gly Pro Ala Gly Pro Pro Gly Leu Pro Gly Thr Thr Ser Leu Phe<br>                          845                        850                        855 | 3018 |
| aca cca cat cca cgg atg ccc gga gaa caa ggg ccc aaa gga gag aag<br>Thr Pro His Pro Arg Met Pro Gly Glu Gln Gly Pro Lys Gly Glu Lys<br>                          860                        865                        870 | 3066 |
| ggc gat cca ggc ctg cct ggg gaa ccg gga ctg cag ggc cgt cct gga<br>Gly Asp Pro Gly Leu Pro Gly Glu Pro Gly Leu Gln Gly Arg Pro Gly<br>875                          880                        885 | 3114 |
| gaa ttg ggg cct cag gga ccc act gga cca ccg ggt gcc aag gga cag<br>Glu Leu Gly Pro Gln Gly Pro Thr Gly Pro Pro Gly Ala Lys Gly Gln<br>890                          895                        900                        905 | 3162 |
| gaa ggt gca cat ggg gct cct gga gca gct gga aac ccc ggt gct ccc<br>Glu Gly Ala His Gly Ala Pro Gly Ala Ala Gly Asn Pro Gly Ala Pro<br>                          910                        915                        920 | 3210 |
| gga cat gtc ggt gcc ccc ggt ccc agt ggc cct cca gga agt gtg ggt<br>Gly His Val Gly Ala Pro Gly Pro Ser Gly Pro Pro Gly Ser Val Gly<br>                          925                        930                        935 | 3258 |
| gct ccc ggc ctc aga ggc acc cca ggg aaa gat ggg gag cgt ggt gag<br>Ala Pro Gly Leu Arg Gly Thr Pro Gly Lys Asp Gly Glu Arg Gly Glu<br>                          940                        945                        950 | 3306 |
| aag ggt gca gcg ggg gaa gaa ggc agc cca ggg cca gtt ggt ccc agg<br>Lys Gly Ala Ala Gly Glu Glu Gly Ser Pro Gly Pro Val Gly Pro Arg<br>955                          960                        965 | 3354 |
| gga gat cct ggt gct cct ggg ctc cct ggg ccg ccc gga aaa ggg aag<br>Gly Asp Pro Gly Ala Pro Gly Leu Pro Gly Pro Pro Gly Lys Gly Lys<br>970                          975                        980                        985 | 3402 |
| gat gga gag ccg gga ctc cgt gga tca cct gga ctc cct gga ccc cta<br>Asp Gly Glu Pro Gly Leu Arg Gly Ser Pro Gly Leu Pro Gly Pro Leu<br>                          990                        995                        1000 | 3450 |
| gga acc aag gct gct tgc gga aaa gtc aga ggg tca gaa aac tgt gca<br>Gly Thr Lys Ala Ala Cys Gly Lys Val Arg Gly Ser Glu Asn Cys Ala<br>                          1005                      1010                      1015 | 3498 |
| ctg gga ggg caa tgt gtt aag ggg gat cga gga gct cct ggg atc cct<br>Leu Gly Gly Gln Cys Val Lys Gly Asp Arg Gly Ala Pro Gly Ile Pro<br>                          1020                      1025                      1030 | 3546 |
| ggt tct cct ggc agc cgt ggt gac cca ggc att ggg gtt gct ggc cct<br>Gly Ser Pro Gly Ser Arg Gly Asp Pro Gly Ile Gly Val Ala Gly Pro<br>1035                      1040                      1045 | 3594 |
| cct ggc cct tcc gga cca cca gga gac aaa gga tcc ccg gga tca cga<br>Pro Gly Pro Ser Gly Pro Pro Gly Asp Lys Gly Ser Pro Gly Ser Arg<br>1050                      1055                      1060                      1065 | 3642 |
| ggc tta cct gga ttc cct ggc ccc cag ggc cca gcc ggc cgg gac ggt<br>Gly Leu Pro Gly Phe Pro Gly Pro Gln Gly Pro Ala Gly Arg Asp Gly | 3690 |

-continued

```
              1070           1075           1080
gca cca gga aat cca gga gaa aga ggg cct cct ggc aag ccg ggc ctc        3738
Ala Pro Gly Asn Pro Gly Glu Arg Gly Pro Pro Gly Lys Pro Gly Leu
            1085           1090           1095 tct tca cta ctg tct cca ggg gac ata aat ctc ttg gct aag gat gtg        3786
Ser Ser Leu Leu Ser Pro Gly Asp Ile Asn Leu Leu Ala Lys Asp Val
        1100           1105           1110 tgc aat gac tgc cct cct ggc ccc cca ggc ctc cct ggt cta cca ggt        3834
Cys Asn Asp Cys Pro Pro Gly Pro Pro Gly Leu Pro Gly Leu Pro Gly
    1115           1120           1125 ttt aaa ggg gac aaa ggt gtc cca gga aag cca ggg aga gaa ggc aca        3882
Phe Lys Gly Asp Lys Gly Val Pro Gly Lys Pro Gly Arg Glu Gly Thr
1130           1135           1140           1145 gaa ggg aaa aag gga gag gct ggg cct cca ggc cta cca ggg ccc cca        3930
Glu Gly Lys Lys Gly Glu Ala Gly Pro Pro Gly Leu Pro Gly Pro Pro
            1150           1155           1160 gga ata gct gga cca cag gga agt caa gga gaa cgt ggt gca gat ggt        3978
Gly Ile Ala Gly Pro Gln Gly Ser Gln Gly Glu Arg Gly Ala Asp Gly
        1165           1170           1175 gag gtt ggg cag aaa ggt gat cag ggt cat cct gga gtt cca ggt ttc        4026
Glu Val Gly Gln Lys Gly Asp Gln Gly His Pro Gly Val Pro Gly Phe
    1180           1185           1190 atg ggg ccc cca ggg aac ccc ggg cca cca ggg gca gat gga att gca        4074
Met Gly Pro Pro Gly Asn Pro Gly Pro Pro Gly Ala Asp Gly Ile Ala
1195           1200           1205 gga gct gct gga cca cca gga atc caa ggg tca cct ggg aaa gaa ggc        4122
Gly Ala Ala Gly Pro Pro Gly Ile Gln Gly Ser Pro Gly Lys Glu Gly
1210           1215           1220           1225 cct cct ggc ccc caa ggc cca tct gga tta ccc gga atc cca gga gaa        4170
Pro Pro Gly Pro Gln Gly Pro Ser Gly Leu Pro Gly Ile Pro Gly Glu
            1230           1235           1240 gaa ggc aaa gag ggc aga gat gga aag ccg ggt ccc cct gga gag ccg        4218
Glu Gly Lys Glu Gly Arg Asp Gly Lys Pro Gly Pro Pro Gly Glu Pro
        1245           1250           1255 ggc aaa gca gga gag cca ggt cta cca gga cca gag ggt gcc cga ggc        4266
Gly Lys Ala Gly Glu Pro Gly Leu Pro Gly Pro Glu Gly Ala Arg Gly
    1260           1265           1270 cca cct ggc ttc aag gga cac aca ggc gat tct ggt gca ccc ggt ccc        4314
Pro Pro Gly Phe Lys Gly His Thr Gly Asp Ser Gly Ala Pro Gly Pro
1275           1280           1285 cgg gga gag tct ggt gcc atg ggg ctt cct ggt cag gaa ggg tta cca        4362
Arg Gly Glu Ser Gly Ala Met Gly Leu Pro Gly Gln Glu Gly Leu Pro
1290           1295           1300           1305 gga aaa gat ggt gac act gga ccc act ggg cca cag ggt ccc caa gga        4410
Gly Lys Asp Gly Asp Thr Gly Pro Thr Gly Pro Gln Gly Pro Gln Gly
            1310           1315           1320 cca agg ggc cca ccg ggc aag aat gga tca ccg gga tct cca gga gag        4458
Pro Arg Gly Pro Pro Gly Lys Asn Gly Ser Pro Gly Ser Pro Gly Glu
        1325           1330           1335 cct ggc cct tca gga acc cct ggc cag aaa gga agc aaa ggg gaa aat        4506
Pro Gly Pro Ser Gly Thr Pro Gly Gln Lys Gly Ser Lys Gly Glu Asn
    1340           1345           1350 ggc agc cca gga ctt cct ggc ttc ctg ggt ccc cgt ggg cct ccg gga        4554
Gly Ser Pro Gly Leu Pro Gly Phe Leu Gly Pro Arg Gly Pro Pro Gly
1355           1360           1365 gaa cca gga gag aaa gga gtc cca ggc aag gag ggg gtc cct ggg aag        4602
Glu Pro Gly Glu Lys Gly Val Pro Gly Lys Glu Gly Val Pro Gly Lys
1370           1375           1380           1385 cct gga gag cct gga ttc aaa gga gaa agg gga gat cct ggg atc aaa        4650
```

| | | |
|---|---|---|
| Pro Gly Glu Pro Gly Phe Lys Gly Glu Arg Gly Asp Pro Gly Ile Lys | | |
| 1390 | 1395 | 1400 |

```
ggt gac aaa gga cct cct ggt gga aaa ggc cag cct ggg gac cct gga      4698
Gly Asp Lys Gly Pro Pro Gly Gly Lys Gly Gln Pro Gly Asp Pro Gly
         1405                1410                1415 atc cca ggc cac aaa ggc cac aca ggc ctg atg ggt ccc caa gga cta      4746
Ile Pro Gly His Lys Gly His Thr Gly Leu Met Gly Pro Gln Gly Leu
    1420                1425                1430 cct ggg gag aat gga cca gtt gga ccc cca ggg cct cca ggc cag ccg      4794
Pro Gly Glu Asn Gly Pro Val Gly Pro Pro Gly Pro Pro Gly Gln Pro
   1435                1440                1445 gga ttt cca gga ctg agg ggg gag tct cca tcc atg gaa acc ctg cgt      4842
Gly Phe Pro Gly Leu Arg Gly Glu Ser Pro Ser Met Glu Thr Leu Arg
1450                1455                1460                1465 cgg ctt att caa gaa gag ctg ggg aag cag ctt gaa acc aga ctc gcc      4890
Arg Leu Ile Gln Glu Glu Leu Gly Lys Gln Leu Glu Thr Arg Leu Ala
             1470                1475                1480 tac ctc ctg gcc cag atg ccc ccg gcg tac atg aag tca tct caa ggc      4938
Tyr Leu Leu Ala Gln Met Pro Pro Ala Tyr Met Lys Ser Ser Gln Gly
         1485                1490                1495 aga cct ggg ccc cca ggg ccc cct gga aaa gat ggg ctt cca ggc cgg      4986
Arg Pro Gly Pro Pro Gly Pro Pro Gly Lys Asp Gly Leu Pro Gly Arg
    1500                1505                1510 gcc ggc ccc atg ggg gag cca ggt cgt cct ggg cag ggg ggt ctg gaa      5034
Ala Gly Pro Met Gly Glu Pro Gly Arg Pro Gly Gln Gly Gly Leu Glu
   1515                1520                1525 gga ccc tct gga ccc ata ggt ccc aaa ggt gag cga gga gcc aaa ggt      5082
Gly Pro Ser Gly Pro Ile Gly Pro Lys Gly Glu Arg Gly Ala Lys Gly
1530                1535                1540                1545 gac cca ggt gca cct gga gtt ggc ctc cga ggc gag atg gga ccc cct      5130
Asp Pro Gly Ala Pro Gly Val Gly Leu Arg Gly Glu Met Gly Pro Pro
             1550                1555                1560 gga atc cca ggt caa ccc ggg gaa cct ggc tat gct aaa gat gga ctt      5178
Gly Ile Pro Gly Gln Pro Gly Glu Pro Gly Tyr Ala Lys Asp Gly Leu
         1565                1570                1575 cct ggg atc cct ggc cct caa ggg gag aca gga cca gct gga cat cct      5226
Pro Gly Ile Pro Gly Pro Gln Gly Glu Thr Gly Pro Ala Gly His Pro
    1580                1585                1590 ggc ctc cca gga cct ccc ggt ccc cca ggc caa tgt gac cct tcc cag      5274
Gly Leu Pro Gly Pro Pro Gly Pro Pro Gly Gln Cys Asp Pro Ser Gln
   1595                1600                1605 tgt gcc tac ttc gcc agc ctt gct gcc cgg ccg ggt aat gtg aag ggt      5322
Cys Ala Tyr Phe Ala Ser Leu Ala Ala Arg Pro Gly Asn Val Lys Gly
1610                1615                1620                1625 ccc taaaggactc tggaaagcca aagactgca gtggatttct gaaacttgaa            5375
Pro ctcagagccc agtgggaagc cagaggtctt gaaagacttc agccatgtgt tccttttttt    5435
tttctttctt ttatcgtttg cttttgtttt tattttcttg agagacctca aaattattaa    5495
atccaacaga cgctgccggt cggtcagatt attattaata ttattgttgt tgttaattat    5555
tattattatt tcatatgctg atgctttgtg agttcttttc cactccttta aagttgggaa    5615
aacttgattc gtgggcagg agattgtttc ttcattcttc tgacagcccc catctgacgc     5675
gtaactgccc atttttaagga aactcttggt gctacaaaac cctgaccaga cacttggcaa   5735
atttacctct ttcttcaaaa gaaaaacttt aagaaaatga gccaatgggc ttcattctca    5795
gtcatgcccg gagatcaccc aggagaaata atacaaacac caccactgtc cagagagagt   5855
aaagaagcag aaagagaaag aatttgcaac catgaggaat gttcccacct cccgacggga    5915
```

-continued

```
cgtgcatttg gaaaacacag aatcagccct cagggtgcac tccagccacc tcagtgctct    5975
aagctcacag aagtgaaata atgtctgtgg gttggcaatg gctttgtggg atcatatgtc    6035
ttggccaaag atgggaaaac ctatgttgaa gaggcagccc ttgagtgtta atttgtcttc    6095
taaactgtgt aaggccccctt caagttcctc ttgttggttt caattatatt aattataaaa   6155
caagtggatg tggtgaccat ccacttgtgt ttccctaatg atgggcagtt ggccagggca    6215
ctgaccagag ctgggaaatt tgtatctcca aggcggctct gtctctgaaa taaatggcat    6275
caagtgcatg tgtgtatgcg acatgccctg cctgaacagg tgctcaataa atccaagttt    6335
ccttctcttg aaaaaaa                                                    6352
```

<210> SEQ ID NO 2
<211> LENGTH: 1626
<212> TYPE: PRT
<213> ORGANISM: Homo sapiens

<400> SEQUENCE: 2

```
Met Ala Gly Leu Arg Gly Asn Ala Val Ala Gly Leu Leu Trp Met Leu
  1               5                  10                  15

Leu Leu Trp Ser Gly Gly Gly Cys Gln Ala Gln Arg Ala Gly Cys
             20                  25                  30

Lys Ser Val His Tyr Asp Leu Val Phe Leu Leu Asp Thr Ser Ser Ser
             35                  40                  45

Val Gly Lys Glu Asp Phe Glu Lys Val Arg Gln Trp Val Ala Asn Leu
  50                  55                  60

Val Asp Thr Phe Glu Val Gly Pro Asp Arg Thr Arg Val Gly Val Val
 65                  70                  75                  80

Arg Tyr Ser Asp Arg Pro Thr Thr Ala Phe Glu Leu Gly Leu Phe Gly
                 85                  90                  95

Ser Gln Glu Glu Val Lys Ala Ala Ala Arg Arg Leu Ala Tyr His Gly
            100                 105                 110

Gly Asn Thr Asn Thr Gly Asp Ala Leu Arg Tyr Ile Thr Ala Arg Ser
            115                 120                 125

Phe Ser Pro His Ala Gly Gly Arg Pro Arg Asp Arg Ala Tyr Lys Gln
        130                 135                 140

Val Ala Ile Leu Leu Thr Asp Gly Arg Ser Gln Asp Leu Val Leu Asp
145                 150                 155                 160

Ala Ala Ala Ala Ala His Arg Ala Gly Ile Arg Ile Phe Ala Val Gly
                165                 170                 175

Val Gly Glu Ala Leu Lys Glu Glu Leu Glu Glu Ile Ala Ser Glu Pro
            180                 185                 190

Lys Ser Ala His Val Phe His Val Ser Asp Phe Asn Ala Ile Asp Lys
        195                 200                 205

Ile Arg Gly Lys Leu Arg Arg Arg Leu Cys Glu Asn Val Leu Cys Pro
    210                 215                 220

Ser Val Arg Val Glu Gly Asp Arg Phe Lys His Thr Asn Gly Thr
225                 230                 235                 240

Lys Glu Ile Thr Gly Phe Asp Leu Met Asp Leu Phe Ser Val Lys Glu
                245                 250                 255

Ile Leu Gly Lys Arg Glu Asn Gly Ala Gln Ser Ser Tyr Val Arg Met
            260                 265                 270

Gly Ser Phe Pro Val Val Gln Ser Thr Glu Asp Val Phe Pro Gln Gly
        275                 280                 285
```

```
Leu Pro Asp Glu Tyr Ala Phe Val Thr Thr Phe Arg Phe Lys Thr
290                 295                 300

Ser Arg Lys Glu Asp Trp Tyr Ile Trp Gln Val Ile Asp Gln Tyr Gly
305                 310                 315                 320

Ile Pro Gln Val Ser Ile Arg Leu Asp Gly Glu Asn Lys Ala Val Glu
                325                 330                 335

Tyr Asn Ala Val Gly Ala Met Lys Asp Ala Val Arg Val Val Phe Arg
                340                 345                 350

Gly Ser Arg Val Asn Asp Leu Phe Asp Arg Asp Trp His Lys Met Ala
            355                 360                 365

Leu Ser Ile Gln Ala Gln Asn Val Ser Leu His Ile Asp Cys Ala Leu
370                 375                 380

Val Gln Thr Leu Pro Ile Glu Glu Arg Glu Asn Ile Asp Ile Gln Gly
385                 390                 395                 400

Lys Thr Val Ile Gly Lys Arg Leu Tyr Asp Ser Val Pro Ile Asp Phe
                405                 410                 415

Asp Leu Gln Arg Ile Val Ile Tyr Cys Asp Ser Arg His Ala Glu Leu
                420                 425                 430

Glu Thr Cys Cys Asp Ile Pro Ser Gly Pro Cys Gln Val Thr Val Val
            435                 440                 445

Thr Glu Pro Pro Pro Pro Pro Pro Gln Arg Pro Pro Thr Pro Gly
450                 455                 460

Ser Glu Gln Ile Gly Phe Leu Lys Thr Ile Asn Cys Ser Cys Pro Ala
465                 470                 475                 480

Gly Glu Lys Gly Glu Met Gly Val Ala Gly Pro Met Gly Leu Pro Gly
                485                 490                 495

Pro Lys Gly Asp Ile Gly Ala Ile Gly Pro Val Gly Ala Pro Gly Pro
            500                 505                 510

Lys Gly Glu Lys Gly Asp Val Gly Ile Gly Pro Phe Gly Gln Gly Glu
            515                 520                 525

Lys Gly Glu Lys Gly Ser Leu Gly Leu Pro Gly Pro Pro Gly Arg Asp
530                 535                 540

Gly Ser Lys Gly Met Arg Gly Glu Pro Gly Leu Gly Glu Pro Gly
545                 550                 555                 560

Leu Pro Gly Glu Val Gly Met Arg Gly Pro Gln Gly Pro Pro Gly Leu
                565                 570                 575

Pro Gly Pro Pro Gly Arg Val Gly Ala Pro Gly Leu Gln Gly Glu Arg
            580                 585                 590

Gly Glu Lys Gly Thr Arg Gly Glu Lys Gly Glu Arg Gly Leu Asp Gly
        595                 600                 605

Phe Pro Gly Lys Pro Gly Asp Thr Gly Gln Gln Gly Arg Pro Gly Pro
610                 615                 620

Ser Gly Val Ala Gly Pro Gln Gly Glu Lys Gly Asp Val Gly Pro Ala
625                 630                 635                 640

Gly Pro Pro Gly Val Pro Gly Ser Val Val Gln Gln Glu Gly Leu Lys
                645                 650                 655

Gly Glu Gln Gly Ala Pro Gly Pro Arg Gly His Gln Gly Ala Pro Gly
            660                 665                 670

Pro Pro Gly Ala Arg Gly Pro Ile Gly Pro Glu Gly Arg Asp Gly Pro
        675                 680                 685

Pro Gly Leu Gln Gly Leu Arg Gly Lys Lys Gly Asp Met Gly Pro Pro
690                 695                 700

Gly Ile Pro Gly Leu Leu Gly Leu Gln Gly Pro Pro Gly Pro Pro Gly
```

-continued

```
            705                 710                 715                 720
Val Pro Gly Pro Pro Gly Pro Gly Gly Ser Pro Gly Leu Pro Gly Glu
                725                 730                 735
Ile Gly Phe Pro Gly Lys Pro Gly Pro Pro Gly Pro Thr Gly Pro Pro
                740                 745                 750
Gly Lys Asp Gly Pro Asn Gly Pro Pro Gly Pro Pro Gly Thr Lys Gly
                755                 760                 765
Glu Pro Gly Glu Arg Gly Glu Asp Gly Leu Pro Gly Lys Pro Gly Leu
                770                 775                 780
Arg Gly Glu Ile Gly Glu Gln Gly Leu Ala Gly Arg Pro Gly Glu Lys
785                 790                 795                 800
Gly Glu Ala Gly Leu Pro Gly Ala Pro Gly Phe Pro Gly Val Arg Gly
                805                 810                 815
Glu Lys Gly Asp Gln Gly Glu Lys Gly Glu Leu Gly Leu Pro Gly Leu
                820                 825                 830
Lys Gly Asp Arg Gly Glu Lys Gly Glu Ala Gly Pro Ala Gly Pro Pro
                835                 840                 845
Gly Leu Pro Gly Thr Thr Ser Leu Phe Thr Pro His Pro Arg Met Pro
850                 855                 860
Gly Glu Gln Gly Pro Lys Gly Glu Lys Gly Asp Pro Gly Leu Pro Gly
865                 870                 875                 880
Glu Pro Gly Leu Gln Gly Arg Pro Gly Glu Leu Gly Pro Gln Gly Pro
                885                 890                 895
Thr Gly Pro Pro Gly Ala Lys Gly Gln Glu Gly Ala His Gly Ala Pro
                900                 905                 910
Gly Ala Ala Gly Asn Pro Gly Ala Pro Gly His Val Gly Ala Pro Gly
                915                 920                 925
Pro Ser Gly Pro Pro Gly Ser Val Gly Ala Pro Gly Leu Arg Gly Thr
                930                 935                 940
Pro Gly Lys Asp Gly Glu Arg Gly Glu Lys Gly Ala Ala Gly Glu Glu
945                 950                 955                 960
Gly Ser Pro Gly Pro Val Gly Pro Arg Gly Asp Pro Gly Ala Pro Gly
                965                 970                 975
Leu Pro Gly Pro Pro Gly Lys Gly Lys Asp Gly Glu Pro Gly Leu Arg
                980                 985                 990
Gly Ser Pro Gly Leu Pro Gly Pro Leu Gly Thr Lys Ala Ala Cys Gly
                995                 1000                1005
Lys Val Arg Gly Ser Glu Asn Cys Ala Leu Gly Gly Gln Cys Val Lys
                1010                1015                1020
Gly Asp Arg Gly Ala Pro Gly Ile Pro Gly Ser Pro Gly Ser Arg Gly
1025                1030                1035                1040
Asp Pro Gly Ile Gly Val Ala Gly Pro Pro Gly Pro Ser Gly Pro Pro
                1045                1050                1055
Gly Asp Lys Gly Ser Pro Gly Ser Arg Gly Leu Pro Gly Phe Pro Gly
                1060                1065                1070
Pro Gln Gly Pro Ala Gly Arg Asp Gly Ala Pro Gly Asn Pro Gly Glu
                1075                1080                1085
Arg Gly Pro Pro Gly Lys Pro Gly Leu Ser Ser Leu Ser Pro Gly
                1090                1095                1100
Asp Ile Asn Leu Leu Ala Lys Asp Val Cys Asn Asp Cys Pro Pro Gly
1105                1110                1115                1120
Pro Pro Gly Leu Pro Gly Leu Pro Gly Phe Lys Gly Asp Lys Gly Val
                1125                1130                1135
```

```
Pro Gly Lys Pro Gly Arg Glu Gly Thr Glu Gly Lys Gly Glu Ala
        1140                1145                1150

Gly Pro Pro Gly Leu Pro Gly Pro Gly Ile Ala Gly Pro Gln Gly
        1155                1160                1165

Ser Gln Gly Glu Arg Gly Ala Asp Gly Glu Val Gly Gln Lys Gly Asp
        1170                1175                1180

Gln Gly His Pro Gly Val Pro Gly Phe Met Gly Pro Gly Asn Pro
1185                1190                1195                1200

Gly Pro Pro Gly Ala Asp Gly Ile Ala Gly Ala Gly Pro Pro Gly
        1205                1210                1215

Ile Gln Gly Ser Pro Gly Lys Glu Gly Pro Pro Gly Pro Gln Gly Pro
        1220                1225                1230

Ser Gly Leu Pro Gly Ile Pro Gly Glu Glu Gly Lys Glu Gly Arg Asp
        1235                1240                1245

Gly Lys Pro Gly Pro Pro Gly Glu Pro Gly Lys Ala Gly Glu Pro Gly
        1250                1255                1260

Leu Pro Gly Pro Glu Gly Ala Arg Gly Pro Pro Gly Phe Lys Gly His
1265                1270                1275                1280

Thr Gly Asp Ser Gly Ala Pro Gly Pro Arg Gly Glu Ser Gly Ala Met
                1285                1290                1295

Gly Leu Pro Gly Gln Glu Gly Leu Pro Gly Lys Asp Gly Asp Thr Gly
                1300                1305                1310

Pro Thr Gly Pro Gln Gly Pro Gln Gly Arg Gly Pro Pro Gly Lys
        1315                1320                1325

Asn Gly Ser Pro Gly Ser Pro Gly Glu Pro Gly Pro Ser Gly Thr Pro
        1330                1335                1340

Gly Gln Lys Gly Ser Lys Gly Glu Asn Gly Ser Pro Gly Leu Pro Gly
1345                1350                1355                1360

Phe Leu Gly Pro Arg Gly Pro Pro Gly Glu Pro Gly Glu Lys Gly Val
                1365                1370                1375

Pro Gly Lys Glu Gly Val Pro Gly Lys Pro Gly Glu Pro Gly Phe Lys
        1380                1385                1390

Gly Glu Arg Gly Asp Pro Gly Ile Lys Gly Asp Lys Gly Pro Pro Gly
        1395                1400                1405

Gly Lys Gly Gln Pro Gly Asp Pro Gly Ile Pro Gly His Lys Gly His
        1410                1415                1420

Thr Gly Leu Met Gly Pro Gln Gly Leu Pro Gly Glu Asn Gly Pro Val
1425                1430                1435                1440

Gly Pro Pro Gly Pro Pro Gly Gln Pro Gly Phe Pro Gly Leu Arg Gly
                1445                1450                1455

Glu Ser Pro Ser Met Glu Thr Leu Arg Arg Leu Ile Gln Glu Glu Leu
        1460                1465                1470

Gly Lys Gln Leu Glu Thr Arg Leu Ala Tyr Leu Leu Ala Gln Met Pro
        1475                1480                1485

Pro Ala Tyr Met Lys Ser Ser Gln Gly Arg Pro Gly Pro Pro Gly Pro
        1490                1495                1500

Pro Gly Lys Asp Gly Leu Pro Gly Arg Ala Gly Pro Met Gly Glu Pro
1505                1510                1515                1520

Gly Arg Pro Gly Gln Gly Gly Leu Glu Gly Pro Ser Gly Pro Ile Gly
                1525                1530                1535

Pro Lys Gly Glu Arg Gly Ala Lys Gly Asp Pro Gly Ala Pro Gly Val
        1540                1545                1550
```

```
Gly Leu Arg Gly Glu Met Gly Pro Pro Gly Ile Pro Gly Gln Pro Gly
        1555                1560                1565

Glu Pro Gly Tyr Ala Lys Asp Gly Leu Pro Gly Ile Pro Gly Pro Gln
    1570                1575                1580

Gly Glu Thr Gly Pro Ala Gly His Pro Gly Leu Pro Gly Pro Pro Gly
1585                1590                1595                1600

Pro Pro Gly Gln Cys Asp Pro Ser Gln Cys Ala Tyr Phe Ala Ser Leu
        1605                1610                1615

Ala Ala Arg Pro Gly Asn Val Lys Gly Pro
        1620                1625

<210> SEQ ID NO 3
<211> LENGTH: 4881
<212> TYPE: DNA
<213> ORGANISM: Homo sapiens

<400> SEQUENCE: 3
atggccggcc tccgagggaa cgctgtggct ggcctcctct ggatgctgct gctgtggagt     60 ggggcggcg  gctgccaggc tcagcgggca ggttgcaaaa gtgtccacta cgatctggtc    120
ttcctcctgg acacctcctc cagcgtgggc aaggaggact ttgagaaggt ccggcagtgg    180
gtggccaacc tggtggacac cttcgaggtg gcccccgacc gcacccgtgt ggggtcgtg    240 cgctacagcg accggcccac cacggccttc gagttgggac tctttggctc gcaggaggag    300
gtcaaggcgg ctgcccggcg tctcgcctac acgggggca acaccaacac gggagacgcg    360
ctccgctaca tcacggcccg cagcttctcc ccacacgccg gcggccgccc cagggaccgc    420
gcctacaagc aggtggccat cctgctcacc gacggccgca gccaggacct ggtgctggac    480 gccgcggcg  cagcccaccg cgctggcatc cgcatctttg ccgtgggcgt gggcgaggca    540
ctcaaggagg agctggagga gatcgcctca gagcccaagt ccgcccacgt cttccacgtg    600
tccgacttca tgccatcga  caagatccgg gcaagctgc ggcgccgtct tgtgaaaat     660 gtgctctgtc ctagcgttcg tgtagaagga gatcgcttta agcacaccaa tggaggaacc    720
aaggaaatca caggttttga cctgatggat tgttcagtg tgaaggaaat cttggggaag    780
agagagaatg gagctcagag ttcctatgta cggatgggat ccttccctgt ggtgcaaagt    840
actgaggatg tgttcccca ggtttacct gatgagtacg cctttgtcac aaccttccgg    900
ttcaggaaaa cctctcggaa ggaagactgg tatatctggc aggtcatcga ccagtacggc    960
atcccacagg tctccatccg gctggatggt gaaaacaagg cagtcgagta caacgctgtg   1020
ggtgccatga agatgctgtg cagggtggtc ttccgaggtt ctcgggtcaa tgacctcttt   1080
gaccgggact ggcacaagat ggccctgagc atccaggccc agaacgtctc cctgcacatt   1140
gactgtgcgc tggtgcagac actacccatc gaggaacggg agaacattga catccagggc   1200
aagactgtga ttggcaagcg cctctacgac agtgtgccca ttgactttga cctacagcgg   1260
attgtgatct attgtgactc gagacacgca gaattggaga cttgttgtga tatcccctcg   1320
ggtccgtgcc aggtgaccgt ggtgacagag cctccacctc accccccacc ccagcggcct   1380 cccacccag  gcagtgaaca gattgggttt ttgaagacca tcaactgctc ctgcccagct   1440
ggagagaagg gtgaaatggg agttgctggc cccatgggc tccctggtcc aaagggagac   1500
ataggagcca ttgggccggt tggcgctcct ggacctaagg gagagaaagg tgatgtgggc   1560
ataggacctt ttggccaagg ggaaaagggt gaaaagggtt ccctgggcct gcccggcccc   1620
cctgggagag acggcagcaa aggcatgaga ggggagccag gagagctggg agagccgggg   1680
```

-continued

```
ctgccgggtg aggtcggcat gcggggggccc caaggaccac ctggactccc cggacctcct  1740
ggacgtgtcg gagctcctgg tctccaagga gaacgaggtg aaaagggaac tcgaggagaa  1800
aagggagagc gaggcctgga tggattccct gggaagcctg gggacacagg acagcagggc  1860
aggcccggcc cttctggtgt ggcaggaccc cagggagaaa agggtgacgt gggacctgcg  1920
gggccacctg gtgtaccagg ctcagtggtg cagcaagagg gcttgaaagg gaacaggga  1980
gctccaggac ccagaggtca ccaaggcgcc cccggtcctc caggagctcg ggtccaata  2040
ggcccagaag gcagggatgg acctcctggt ttgcaaggtc tccgagggaa gaaaggtgac  2100
atgggaccac ctggaatccc tggattgctg ggctgcagg gccctccagg accccctggt  2160
gtcccaggcc cccctggacc gggaggttct ccggggtttgc ctggagagat cggcttcccg  2220
ggaaagcctg gacctcctgg gcccacggga cccctggaa aggacgggcc aaatggacca  2280
ccaggtccgc caggaaccaa gggagaacca ggagaaagag gggaagatgg tctgcctgga  2340
aaaccaggcc ttcggggaga aattggggag cagggcctgg caggccgacc tggagagaag  2400
ggagaagcag gcctcccagg ggctccaggc ttcccaggtg tgagaggaga gaaaggagac  2460
cagggagaaa aaggtgaact gggacttcca ggactgaaag gtgaccgagg tgaaaagggt  2520
gaagctggtc ctgcaggccc tcccgggtta cctggaacta catccctgtt cacaccacat  2580
ccacggatgc ccggagaaca agggcccaaa ggagagaagg gcgatccagg cctgcctggg  2640
gaaccgggac tgcagggccg tcctggagaa ttggggcctc agggacccac tggaccaccg  2700
ggtgccaagg acaggaagg tgcacatggg gctcctggag cagctggaaa ccccggtgct  2760
cccggacatg tcggtgcccc cggtcccagt ggccctccag gaagtgtggg tgctcccggc  2820
ctcagaggca ccccagggaa agatggggag cgtggtgaga agggtgcagc gggggaagaa  2880
ggcagcccag ggccagttgg tcccaggggga gatcctggtg ctcctgggct ccctgggccg  2940
cccggaaaag ggaaggatgg agagccggga ctccgtggat cacctggact ccctggaccc  3000
ctaggaacca aggctgcttg cggaaaagtc agagggtcag aaaactgtgc actgggaggg  3060
caatgtgtta aggggatcg aggagctcct gggatccctg gttctcctgg cagccgtggt  3120
gacccaggca ttggggttgc tggccctcct ggcccttccg gaccaccagg agacaaagga  3180
tccccgggat cacgaggctt acctggattc cctggccccc agggcccagc cggccgggac  3240
ggtgcaccag gaaatccagg agaaagaggg cctcctggca gccgggcct ctcttcacta  3300
ctgtctccag gggacataaa tctcttggct aaggatgtgt gcaatgactg ccctcctggc  3360
cccccaggcc tccctggtct accaggtttt aaaggggaca aaggtgtccc aggaaagcca  3420
gggagagaag gcacagaagg gaaaagggga gaggctgggc ctccaggcct accagggccc  3480
ccaggaatag ctgaccaca gggaagtcaa ggagaacgtg gtgcagatgg tgaggttggg  3540
cagaaaggtg atcagggtca tcctggagtt ccaggtttca tggggccccc agggaacccc  3600
gggccaccag gggcagatgg aattgcagga gctgctggac caccaggaat ccaagggtca  3660
cctgggaaag aaggccctcc tggccccca ggcccatctg gattacccgg aatcccagga  3720
gaagaaggca agagggcag agatggaaag ccggtcccc ctggagagcc gggcaaagca  3780
ggagagccag gtctaccagg accagagggt gcccgaggcc cacctggctt caagggacac  3840
acaggcgatt ctggtgcacc cggtcccgg ggagagtctg tgccatggg gcttcctggt  3900
caggaagggt taccaggaaa agatggtgac actggaccca ctgggccaca gggtccccaa  3960
ggaccaaggg gccaccggg caagaatgga tcaccgggat ctccaggaga gcctggccct  4020
tcaggaaccc ctgccagaa aggaagcaaa ggggaaaatg gcagcccagg acttcctggc  4080
```

```
ttcctgggtc cccgtgggcc tccgggagaa ccaggagaga aaggagtccc aggcaaggag    4140
ggggtccctg ggaagcctgg agagcctgga ttcaaaggag aaagggggaga tcctgggatc    4200 aaaggtgaca aaggacctcc tggtggaaaa ggccagcctg gggaccctgg aatcccaggc    4260
cacaaaggcc acacaggcct gatgggtccc caaggactac ctggggagaa tggaccagtt    4320 ggaccccccag ggcctccagg ccagccggga tttccaggac tgagggggga gtctccatcc    4380
atggaaaccc tgcgtcggct tattcaagaa gagctgggga agcagcttga aaccagactc    4440
gcctacctcc tggcccagat gccccggcg tacatgaagt catctcaagg cagacctggg    4500
cccccagggc ccctggaaa agatgggctt ccaggccggg ccggcccat gggggagcca    4560 ggtcgtcctg ggcaggggg tctggaagga ccctctggac ccataggtcc caaaggtgag    4620
cgaggagcca aaggtgaccc aggtgcacct ggagttggcc tccgaggcga gatgggaccc    4680
cctggaatcc caggtcaacc cggggaacct ggctatgcta aagatggact tcctgggatc    4740
cctggccctc aaggggagac aggaccagct ggacatcctg gcctcccagg acctcccggt    4800
cccccaggcc aatgtgaccc ttcccagtgt gcctacttcg ccagccttgc tgcccggccg    4860
ggtaatgtga agggtcccta a                                                4881
```

COLLAGEN XXII, A NOVEL HUMAN COLLAGEN AND USES THEREOF

RELATED APPLICATIONS

This application claims the benefit of U.S. Provisional Application Ser. No. 60/309,158, filed Jul. 31, 2001, the contents of which are incorporated by reference in their entirety, including drawings.

BACKGROUND OF THE INVENTION

Collagen is the most abundant protein in mammals, constituting a quarter of their total weight. Collagen provides the tensile strength in the connective tissues of all animals and is the major fibrous element of skin, bone, tendon, cartilage, blood vessels, and teeth.

Collagens are classified into several types based on sequence identity and function. Types I, II, & III collagen molecules make up the main fibers of most animal extracellular structures. Type I forms about 90% of the body's collagen and is the primary component of bone, skin and tendons. Type II makes up the major fibers of cartilage. Collagen fibers are arranged in rigid plates in bones, in parallel bundles in tendons, and in a dense meshwork in cartilage. Type I and lesser amounts of type III make up tendons and skin. Type IV collagen molecules make up very fine, unstriated fibers present in basal laminae. Over a dozen other collagen types are known but are less well characterized.

Collagen polypeptide chains are characterized by a core helical domain made up of repeating glycine-X-Y triplets and globular N-terminal and C-terminal domains. Three such chains are wound around one another in a superhelix to generate an individual ropelike collagen molecule.

SUMMARY OF THE INVENTION

The present invention is based, in part, on the discovery of a novel collagen, referred to herein as collagen XXII. The nucleotide sequence of a cDNA encoding collagen XXII is shown in SEQ ID NO:1 and the corresponding amino acid sequence of collagen XXII polypeptide is shown in SEQ ID NO:2. In addition, the nucleotide sequences of the coding region are depicted in SEQ ID NO:3. An alternatively spliced variant of collagen XXII lacks nucleotides 3458–3518 of SEQ ID NO:1 and codes for a protein that lacks amino acids 1005–1024 of SEQ ID NO:2.

Accordingly, in one aspect, the invention features a nucleic acid molecule that encodes a collagen XXII protein or polypeptide, e.g., a biologically active portion of the collagen XXII protein. In one embodiment the isolated nucleic acid molecule encodes a polypeptide having the amino acid sequence of SEQ ID NO:2. In another embodiment, the isolated nucleic acid molecule encodes a polypeptide having the amino acid sequence of SEQ ID NO:2 but lacking amino acids 1005–1024 of SEQ ID NO:2. In other embodiments, the invention provides isolated collagen XXII nucleic acid molecules having the nucleotide sequence shown in SEQ ID NO:1, SEQ ID NO:3, or an alternatively spliced variant thereof. In still other embodiments, the invention provides nucleic acid molecules that are substantially identical (e.g., naturally occurring allelic variants) to the nucleotide sequence shown in SEQ ID NO:1, SEQ ID NO:3, or an alternatively spliced variant thereof. In other embodiments, the invention provides a nucleic acid molecule which hybridizes under a stringency condition described herein to a nucleic acid molecule comprising the nucleotide sequence of SEQ ID NO:1, SEQ ID NO:3, or an alternatively spliced variant thereof, wherein the nucleic acid encodes a full length collagen XXII protein or an active fragment thereof.

In a related aspect, the invention further provides nucleic acid constructs that include a collagen XXII nucleic acid molecule described herein. In certain embodiments, the nucleic acid molecules of the invention are operatively linked to native or heterologous regulatory sequences. Also included, are vectors and host cells containing the collagen XXII nucleic acid molecules of the invention e.g., vectors and host cells suitable for producing collagen XXII nucleic acid molecules and polypeptides.

In another related aspect, the invention provides nucleic acid fragments suitable as primers or hybridization probes for the detection of collagen XXII-encoding nucleic acids.

In still another related aspect, isolated nucleic acid molecules that are antisense to a collagen XXII encoding nucleic acid molecule are provided.

In another aspect, the invention features, collagen XXII polypeptides, and biologically active or antigenic fragments thereof that are useful, e.g., as reagents or targets in assays applicable to treatment and diagnosis of collagen XXII-mediated or -related disorders. In another embodiment, the invention provides collagen XXII polypeptides having a collagen XXII activity described herein. Preferred polypeptides are collagen XXII proteins including at least one collagen domain and, preferably, having a collagen XXII activity, e.g., a collagen XXII activity as described herein.

In other embodiments, the invention provides collagen XXII polypeptides, e.g., a collagen XXII polypeptide having the amino acid sequence shown in SEQ ID NO:2; an amino acid sequence that is substantially identical to the amino acid sequence shown in SEQ ID NO:2, e.g., an amino acid sequence comprising amino acids 1–1004 and 1025–1626 of SEQ ID NO:2; or an amino acid sequence encoded by a nucleic acid molecule having a nucleotide sequence which hybridizes under a stringency condition described herein to a nucleic acid molecule comprising the nucleotide sequence of SEQ ID NO:1, SEQ ID NO:3, or an alternatively spliced variant thereof, wherein the nucleic acid encodes a full length collagen XXII protein or an active fragment thereof.

In a related aspect, the invention further provides nucleic acid constructs which include a collagen XXII nucleic acid molecule described herein.

In a related aspect, the invention provides collagen XXII polypeptides or fragments operatively linked to non-collagen XXII polypeptides to form fusion proteins.

In another aspect, the invention features antibodies and antigen-binding fragments thereof, that react with, or more preferably specifically bind collagen XXII polypeptides or fragments thereof, e.g., a collagen Gly-x-y core domain.

In another aspect, the invention provides methods of screening for compounds that modulate the expression or activity of the collagen XXII polypeptides or nucleic acids.

In still another aspect, the invention provides a process for modulating collagen XXII polypeptide or nucleic acid expression or activity, e.g. using the screened compounds. In certain embodiments, the methods involve treatment of conditions related to aberrant activity or expression of the collagen XXII polypeptides or nucleic acids, such as conditions involving aberrant or deficient tissue strength, e.g., in tissue boundaries, e.g., in myotendonous junctions; joints (e.g., diarthrodial joints, synovial joints), e.g., in the articular cartilage of joints; hair follicles; the cilliary body of the eye; heart valves; epithelial-basement membrane boundaries.

The invention also provides assays for determining the activity of or the presence or absence of collagen XXII polypeptides or nucleic acid molecules in a biological sample, including for disease diagnosis.

In a further aspect, the invention provides methods for evaluating the efficacy of a treatment of a disorder, e.g., a collagen related disorder. The method includes: treating a subject, e.g., a patient or an animal, with a protocol under evaluation (e.g., treating a subject with one or more of: chemotherapy, radiation, and/or a compound identified using the methods described herein); and evaluating the expression of a collagen XXII nucleic acid or polypeptide before and after treatment. A change, e.g., a decrease or increase, in the level of a collagen XXII nucleic acid (e.g., mRNA) or polypeptide after treatment, relative to the level of expression before treatment, is indicative of the efficacy of the treatment of the disorder. The level of collagen XXII nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a collagen XXII nucleic acid (e.g., mRNA) or polypeptide before and after treatment.

In another aspect, the invention features a method of treating a subject. The method includes modulating the level of collagen XXII between a first tissue and a second tissue of the subject. The subject can be a human or a non-human animal, e.g., an animal model for a collagen related disorder, e.g., a connective tissue disorder. In a preferred embodiment, the subject has or is at risk for a collagen XXII related disorder, e.g., a connective tissue disorder, e.g., a disorder of a joint, tendon, cartilage, basement membrane, or other tissue—tissue boundary. While not wanting to be bound by theory, the collagen XXII is believed to promote tensile strength and/or adherence of the two tissues. In one embodiment, collagen XXII is found in nature at the tissue—tissue boundary. In another embodiment, collagen XXII is not normally found in nature at the tissue—tissue boundary.

The level of collagen XXII can be modulated by modulating, e.g., collagen XXII expression (e.g., modulating collagen XXII rate of transcription or mRNA stability), protein levels, or protein activity.

In a preferred embodiment, collagen XXII is increased, e.g., by administering an agent that increases the level of collagen XXII. An agent which increases the level of collagen XXII activity can be one or more of the following: a peptide or protein, e.g., a monoclonal antibody, which stabilizes or assists the binding of collagen XXII to a collagen XXII binding partner; a collagen XXII polypeptide or a functional fragment or analog thereof; a nucleotide sequence encoding a collagen XXII polypeptide or functional fragment or analog thereof; an agent which increases collagen XXII nucleic acid expression; e.g., a small molecule which binds to the promoter region of collagen XXII. In a preferred embodiment, collagen XXII levels are increased by administering, e.g., introducing, a nucleotide sequence encoding a collagen XXII polypeptide or functional fragment or analog thereof, into a particular cell, e.g., a connective tissue cell, in the subject. The nucleotide sequence can be a genomic sequence or a cDNA sequence. The nucleotide sequence can include: a collagen XXII coding region; a promoter sequence, e.g., a promoter sequence from a collagen XXII gene or from another gene; an enhancer sequence; untranslated regulatory sequences, e.g., a 5' untranslated region (UTR), e.g., a 5'UTR from a collagen XXII gene or from another gene, a 3' UTR, e.g., a 3'UTR from a collagen XXII gene or from another gene; a polyadenylation site; an insulator sequence. In another preferred embodiment, the level of collagen XXII protein is increased by increasing the level of expression of an endogenous collagen XXII gene, e.g., by increasing transcription of the collagen XXII gene or increasing collagen XXII mRNA stability. In a preferred embodiment, transcription of the collagen XXII gene is increased by: altering the regulatory sequence of the endogenous collagen XXII gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the collagen XXII gene to be transcribed more efficiently.

In some embodiments, the collagen XXII is increased in conjunction with increasing another collagen type, e.g., any one or more of collagen types I, II, III, or IV.

In a preferred embodiment, collagen XXII which is exogenous to one or two of the tissues is administered.

In another preferred embodiment, collagen XXII can be decreased by administering an agent that inhibits collagen XXII gene expression, mRNA stability, protein production levels and/or activity. An agent that inhibits collagen XXII can be one or more of: a collagen XXII binding protein, e.g., a soluble collagen XXII binding protein that binds and inhibits a collagen XXII activity, e.g., helix forming activity, or inhibits the ability of collagen XXII to interact with a binding partner, e.g., a binding partner that binds to one or more of the non-helical interruption domains; an antibody that specifically binds to the collagen XXII protein, e.g., an antibody that disrupts collagen XXII's ability to form a helix or bind to a binding partner; a mutated inactive collagen XXII or fragment thereof which binds to a collagen XXII but disrupts a collagen XXII activity, e.g., a collagen XXII fragment that is able to form a helix with an endogenous collagen XXII, but lacks the non-helical interruption domains and/or the N-terminal and/or C-terminal globular domains; a collagen XXII nucleic acid molecule that can bind to a cellular collagen XXII nucleic acid sequence, e.g., mRNA, and inhibit expression of the protein, e.g., an antisense molecule or collagen XXII ribozyme; an agent which decreases collagen XXII gene expression, e.g., a small molecule which binds the promoter of collagen XXII; an enzyme that breaks down collagen XXII, e.g., a collagenase, e.g., a collagen XXII specific collagenase. In another preferred embodiment, collagen XXII is inhibited by decreasing the level of expression of an endogenous collagen XXII gene, e.g., by decreasing transcription of the collagen XXII gene. In a preferred embodiment, transcription of the collagen XXII gene can be decreased by: altering the regulatory sequences of the endogenous collagen XXII gene, e.g., by the addition of a negative regulatory sequence (such as a DNA-biding site for a transcriptional repressor), or by the removal of a positive regulatory sequence (such as an enhancer or a DNA-binding site for a transcriptional activator). In another preferred embodiment, the antibody which binds collagen XXII is a monoclonal antibody, e.g., a humanized chimeric or human monoclonal antibody.

In some embodiments, the collagen XXII is decreased in conjunction with decreasing another collagen type, e.g., any one or more of collagen types I, II, III, or IV.

The first tissue and the second tissue can be the same tissue type or they can be different tissue types. For example, the first and second tissue can be bone, connective tissue, (e.g., cartilage, tendon, ligament, basement membranes), muscle (e.g., muscle of the heart, eye, or hair follicle), or epithelial tissue. In a preferred embodiment, the first tissue is muscle and the second tissue is connective tissue, e.g., cartilage, tendon, or basement membrane tissue, bone, or another muscle tissue. In another preferred embodiment, the first tissue is bone and the second tissue is cartilage, ligament, muscle, or another bone tissue. In another preferred embodiment, the first tissue is connective tissue, e.g., a ligament, tendon, cartilage, basement membrane tissue, and the second tissue is a different type of connective tissue, e.g., if the first tissue is basement membrane, the second tissue can be, e.g., a ligament, tendon, or cartilage. In yet another preferred embodiment, the first tissue is epithelial tissue and the second tissue is connective tissue, e.g., a basement membrane tissue. In preferred embodiments, the first and second tissue are present in the skin, heart, eye, joints (e.g., the articular cartilage of joints), or hair follicle of the subject.

In another aspect, the invention features a method of treating a subject who has had, is having, or will have a transplant. As used herein, a transplant encompasses the transfer of a non-artificial (biological) tissue from one area of the body to another, the transfer of a non-artificial tissue from one subject to another, or the transfer of an artificial or semi-artificial implantable device to the body of a subject, e.g., a human or non-human animal. The method includes modulating the level of collagen XXII between a first tissue and a second transplanted tissue or implantable device. The transplanted tissue can be autologous, allogeneic, or xenogeneic.

The level of collagen XXII can be modulated, e.g., increased or decreased, by any of the methods described hereinabove. In some embodiments, the collagen XXII is increased in conjunction with increasing another collagen type, e.g., any one or more of collagen types I, II, III, or IV.

In a preferred embodiment, collagen XXII which is exogenous to one or two of the tissues is administered.

If the transplanted tissue is a non-artificial tissue, the first tissue and the second tissue can be the same tissue type or they can be different tissue types. For example, the first and second tissue can be bone, connective tissue, (e.g., cartilage, tendon, ligament, basement membranes), muscle (e.g., muscle of the heart, eye, or hair follicle), or epithlia. In a preferred embodiment, the first tissue is muscle and the second tissue is connective tissue, e.g., cartilage, tendon, or basement membrane tissue, bone, or another muscle tissue. In another preferred embodiment, the first tissue is bone and the second tissue is cartilage, ligament, muscle, or another bone tissue. In another preferred embodiment, the first tissue is connective tissue, e.g., a ligament, tendon, cartilage, basement membrane tissue, and the second tissue is a different type of connective tissue, e.g., if the first tissue is basement membrane, the second tissue can be, e.g., a ligament, tendon, or cartilage. In yet another embodiment, the first tissue is epithelia and the second tissue is connective tissue, e.g., basement membrane tissue. In preferred embodiments, the transplanted tissue is an eye tissue, e.g., a lens; a heart tissue, e.g., a heart valve; a cartilage tissue, e.g., a tendon; a muscle tissue; a hair follicle; an epithelial tissue, e.g., a skin graft.

In other preferred embodiments, the transplanted device is an artificial device, e.g., a non-biological or semi-biological device (e.g., a device containing biological and non-biological components). For example, the transplanted device can be an artificial joint, e.g., an artificial knee or hip; an artificial eye or portion thereof, e.g., lens; an artificial heart or portion thereof, e.g., a heart valve; an artificial hair follicle; an artificial muscle; an artificial connective tissue, e.g., an artificial cartilage, tendon, ligament, or basement membrane tissue; an artificial bone tissue; an artificial tooth; a limb prosthesis.

In some embodiments, an implantable device described herein is contacted with, e.g., coated with, collagen XXII. The implantable device can be contacted with collagen XXII before, during, and/or after the transplant into the subject.

In some embodiments, the collagen XXII is increased in conjunction with increasing another collagen type, e.g., one or more of collagen type I, II, III, or IV.

In another aspect, the invention features a method of promoting wound repair. The method includes identifying a tissue in need of repair, e.g., a collagenous tissue, e.g., cornea, skin, bone, connective tissue, e.g., cartilage, ligament, tendon or basement membrane; and contacting the tissue with an agent that increases collagen XXII, e.g., an agent described hereinabove. The wound can be caused by trauma (e.g., a connective tissue or muscle tear), an incision, or surgery, e.g., transplant surgery, e.g., heart transplant, lens transplant, joint replacement, hair follicle replacement, skin graft. In preferred embodiments, the wound is present in the eye, e.g., the wound is an incision in the lens, e.g., as a result of lens replacement surgery. In another embodiment, the wound is present in a heart tissue, e.g., a heart valve, e.g., as a result of a heart valve replacement or transplant. In yet another embodiment, the wound is present in a connective tissue, e.g., in a cartilage, tendon, or ligament. In another embodiment, the wound is present in an epithelial tissue, e.g., in the dermis. The wound can also be present in a muscle tissue.

In a preferred embodiment, collagen XXII that is exogenous to the wound tissue is administered. In one embodiment, collagen XXII is normally present in the wound tissue in nature. In another embodiment, collagen XXII is not present in the wound tissue in nature.

In a preferred embodiment, the tissue is an eye tissue. For example, the tissue, e.g., cornea, has been subjected to trauma, e.g., a surgical incision, cornea transplant surgery, LASIK flap reattachment, cataract surgery, laser surgery, keratoplasty, penetrating keratoplasty, posterior lamellar keratoplasty, refractive surgery, cornea reshaping, or treatment of corneal laceration.

In a preferred embodiment, the tissue is a connective tissue, e.g., cartilage, tendon, or ligament. In one embodiment, the tissue has been torn, stretched, or subjected to other trauma.

In a preferred embodiment, the method further includes administration of an adjunctive therapy, e.g., administration of antibiotics. In another embodiment, the collagen XXII is increased in conjunction with another collagen type, e.g., one or more of collagen type I, I, III, or IV.

In another aspect, the invention provides methods for evaluating the efficacy of a therapeutic or prophylactic agent. The method includes: contacting a sample with an agent (e.g., a compound identified using the methods described herein, a cytotoxic agent) and, evaluating the expression of collagen XXII nucleic acid or polypeptide in the sample before and after the contacting step. A change, e.g., a decrease or increase, in the level of collagen XXII nucleic acid (e.g., mRNA) or polypeptide in the sample obtained after the contacting step, relative to the level of expression in the sample before the contacting step, is indicative of the efficacy of the agent. The level of collagen XXII nucleic acid or polypeptide expression can be detected by any method described herein. In a preferred embodiment, the sample includes cells obtained from muscle, tendon, cartilage, hair follicle, ocular cilliary body, or heart tissue.

In further aspect, the invention provides assays for determining the presence or absence of a genetic alteration in a collagen XXII polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a collagen XXII molecule. In one embodiment, the capture probe is a nucleic acid, e.g., a probe complementary to a collagen XXII nucleic acid sequence. In another embodiment, the capture probe is a polypeptide, e.g., an antibody specific for collagen XXII polypeptides. Also featured is a method of analyzing a sample by contacting the sample to the aforementioned array and detecting binding of the sample to the array.

In another aspect, the invention features a biomaterial containing collagen XXII, e.g., a recombinant collagen XXII as described herein, which biomaterial is biocompatible and can be, e.g., implanted in the human body. Examples of collagen XXII containing biomaterials of the invention include prostheses; bioengineered tissue, e.g., for tissue repair, replacement, or to provide support of endogenous tissue where weakness exists; coatings, e.g., to improve biological functionality or biocompatibility of artificial implants; bio-compatible gelatins, gels, paste, strips, sponges, strings, fibers, tubes, and films, e.g., as carriers for drug delivery.

Other features and advantages of the invention will be apparent from the following detailed description, and from the claims.

DESCRIPTION OF THE DRAWINGS

FIGS. 1A–C shows the collagen XXII cDNA sequence (SEQ ID NO:1). The coding sequence of collagen XXII starts at nucleotide 448 (the start site ATG is double underlined) and ends at nucleotide 5325 of SEQ ID NO:1. Nucleotides 3458–3518 of SEQ ID NO:1 (underlined) are absent in an alternatively spliced variant.

FIG. 2 shows the collagen XXII amino acid sequence (SEQ ID NO:2). The shaded area highlights the G-X-Y repeats (triple helix domain). Non-triple helical interruptions are double underlined. A non-triple-helical alternatively spliced interruption is bold and underlined. The predicted signal peptide is bolded.

DETAILED DESCRIPTION

The human collagen XXII sequence (see SEQ ID NO:1, as recited in Example 1), which is approximately 6352 nucleotides long including untranslated regions, contains a predicted methionine-initiated coding sequence of about 4878 nucleotides. The coding sequence encodes a 1626 amino acid protein (see SEQ ID NO:2, as recited in Example 1). An alternatively spliced variant lacks nucleotides 3458–3518 of SEQ ID NO:1 and encodes an amino acid sequence that lacks amino acids 1005–1024 of SEQ ID NO:2.

Human collagen XXII contains the following regions or other structural features: a predicted signal peptide, from about amino acid 1–27 of SEQ ID NO:2; a core helical domain rich in G-X-Y repeats from about amino acid 1479–1603 of SEQ ID NO:2; six non-helical interruptions of the core helical domain at about amino acids 853–864, 1004–1024 (present in alternatively spliced variant), 1097–1119, 1457–1495, 1550–1552, and 1572–1575 of SEQ ID NO:2.

The collagen XXII protein is a member of the broad family of collagens. The term "family" when referring to the protein and nucleic acid molecules of the invention means two or more proteins or nucleic acid molecules having a common structural domain or motif. Collagens are characterized by a central domain rich G-X-Y triple repeats, which domain allows for the formation of collagen triple helix molecules made up of three collagen polypeptide chains wound around each other. Collagens typically have globular N-terminal and C-terminal domains, and the ability to form higher order collagen fibrils and/or fibers. Human collagen XXII described herein shares these characteristics of the collagen superfamily.

Type XXII collagens described herein likely comprise a subfamily of collagens. Type XXII collagens can be naturally or non-naturally occurring and can be from either the same or different species. For example, the collagen XXII subfamily can contain a first protein of human origin as well as other distinct proteins of human origin, or alternatively, can contain homologues of non-human origin, e.g., rat or mouse proteins. Members of the collagen type XXII subfamily can also have common functional characteristics.

As used herein, the term "core helical domain" is an amino acid sequence of at least 300 amino acids, preferably at least 500, 600, 700, 800, 900, or at least 1000 amino acids, that is capable of forming a helical structure. A core helical domain is typically rich in Glycine-X-Y repeats and is also rich in proline residues. A core helical domain can have at least one non-helical sequence interruption. A non-helical sequence interruption is an amino acid sequence of between 3 and 100, preferably between about 3 and 70, more preferably between about 3 and 50, amino acid residues in length, that is present in the core helical domain but that is not predicted to form a helical structure. A collagen XXII described herein can have between one and 15, preferably between 3 and 10, more preferably about 5 or 6 non-helical sequence interruptions that are interspersed throughout the core helical domain but that are not predicted to form a helical structure.

In a preferred embodiment collagen XXII polypeptide or protein has a "core helical domain" of between 500 and 1500, preferably between 700 and 1300, more preferably about 1100 amino acid residues, having between 3 and 10, preferably about 5 or 6, non-helical sequence interruptions. The non-helical sequence interruptions can range in length from 3 to 100 amino acid residues, preferably between 3 and 50 amino acid residues.

To identify the presence of a "helical core domain" domain in a collagen XXII protein sequence, and make the determination that a polypeptide or protein of interest has a particular profile, the amino acid sequence of the protein can be searched against the Pfam database of HMMs (e.g., the Pfam database, release 2.1) using the default parameters (www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

Collagen XXII is expressed primarily at the boundary of muscle and other tissue, e.g., connective tissue. In particular, collagen XXII is expressed in myo-tendonous junctions; beneath the articular cartilage of joints; in the basement membrane of the outer root sheath at the base of hair follicles; in the cilliary body of the eye, e.g., where the muscle of the lens intersects the zonular fibers; in the heart, e.g., where the heart muscles intersect the cartilage ring in the region of the valves. As the collagen XXII polypeptides of the invention may modulate collagen XXII-mediated activities, they may be useful as of for developing novel diagnostic and therapeutic agents for collagen XXII-mediated or related disorders, as described below.

As used herein, a "collagen XXII activity", "biological activity of collagen XXII" or "functional activity of collagen XXII", refers to an activity exerted by a collagen XXII protein, polypeptide or nucleic acid molecule. For example, a collagen XXII activity can be an activity exerted by collagen XXII in a physiological milieu on, e.g., a collagen XXII-responsive cell or tissue, e.g., a cartilage tissue, a muscle tissue, a connective tissue, e.g., a tendon or other muscle-tissue junction in, e.g., a joint, the eye, the heart or the hair follicle. A collagen XXII activity can be determined in vivo or in vitro. In one embodiment, a collagen XXII activity is a direct activity, such as an association with a collagen XXII binding partner. A "target molecule" or "binding partner" is a molecule with which a collagen XXII protein binds or interacts in nature.

A collagen XXII activity can also be an indirect activity, e.g., a cellular signaling activity mediated by interaction of the collagen XXII protein with a collagen XXII receptor. The collagen XXII proteins of the present invention can have one or more of the following activities: (1) forms a helix, e.g., an interrupted helix; (2) forms a triple helix consisting of three collagen XXII polypeptide chains; (3) forms higher order collagen XXII fibrils and/or fibers; (4) forms at least 1, preferably between 3 and 10 non-helical interruptions or domains within the core helical domain; (5) provides tensile strength and/or flexibility to tissue boundaries, e.g., muscle-connective tissue boundaries; (6) provides form to a tissue, e.g., during growth and/or development, (7) separates or anchors cell layers or tissue, e.g., at muscle-tissue junctions, dermal-epidermal junctions, basement membranes that separate epithelial and mesenchymal structures; (8) provides a filtration barrier between tissues; (9) provides transparency, e.g., in the eye; (10) is regulated, in part, by alternative splicing; (11) is recognized by R34 antibody described herein.

Thus, the collagen XXII molecules can act as novel diagnostic targets and therapeutic agents for controlling collagen related disorders or conditions. Examples of such disorders include osteoarthritis; osteogenesis imperfecta; dystrophic epidermolysis bullosa; polymyositis and dermatomyositis ("PM/DM"). Further, as collagen XXII is expressed in muscle-cartilage boundaries in heart valves, collagen XXII or functional fragments thereof may be useful in treating disorders of the heart valve or other regions of the heart, or in making, treating, or maintaining transplantable biological equivalents of the hearts of parts thereof. collagen XXII may serve to increase the success of such transplants, or increase the useful lifetime of the heart and its valves, or increase the success of heart surgeries.

As collagen XXII is expressed in muscle-connective tissue boundaries in the eye, collagen XXII or functional fragments thereof may be useful in treating disorders of the eye, or in making, treating, or maintaining transplantable biological equivalents of the eye of parts thereof. Collagen XXII may serve to increase the success of such transplants, e.g., lens replacements, or increase the useful lifetime of the lens and its attachments, or increase the success of eye surgeries, e.g., to treat surgery induced endophthalmitis.

As collagen XXII is expressed in cartilage, collagen XXII or functional fragments thereof may be useful to treat cartilage-related disorders or conditions, or in making, treating, or maintaining transplantable biological equivalents of the cartilage of parts thereof. Collagen XXII may serve to increase the success of such transplants, or increase the useful lifetime of the cartilage and its articular surface, or increase the success of, e.g., joint surgeries and cartilage replacement.

As collagen XXII is also expressed in tendon and mytendonous junctions, or at junctions of tendons with cartilage or with perichondrium or with bone, collagen XXII or functional fragments thereof may be used to treat tendons or muscle disorders or conditions, or to make, treat, or maintain transplantable biological equivalents of the tendons or muscles or of parts thereof. Collagen XXII may serve to increase the success of such transplants, or increase the useful lifetime of the tendons or the junctions of tendons with muscle or tendons with cartilage, or increase the success of joint surgeries involving tendons, or of tendon replacement or repair.

As collagen XXII is also expressed in the hair follicle, collagen XXII or functional fragments thereof may be used to treat hair related conditions, e.g., hair loss. In transplantable biological equivalents of the hair follicle of parts thereof, collagen XXII may serve to increase the success of such transplants, or increase the growth or stability of the hair follicle, or extend the anagen phase of the hair cycle. Downregulation of collagen XXII may destabilize the integrity of the follicle in the dermis and result in hair loss.

The collagen XXII protein, fragments thereof, and derivatives and other variants of the sequence in SEQ ID NO:2 thereof are collectively referred to as "polypeptides or proteins of the invention" or "collagen XXII polypeptides or proteins". Nucleic acid molecules encoding such polypeptides or proteins are collectively referred to as "nucleic acids of the invention" or "collagen XXII nucleic acids." Collagen XXII molecules refer to collagen XXII nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid)

in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1 or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a collagen XXII protein. The gene can optionally further include non-coding sequences, e.g., regulatory sequences and introns. Preferably, a gene encodes a mammalian collagen XXII protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of collagen XXII protein is at least 10% pure. In a preferred embodiment, the preparation of collagen XXII protein has less than about 30%, 20%, 10% and more preferably 5% (by dry weight), of non-collagen XXII protein (also referred to herein as a "contaminating protein"), or of chemical precursors or non-collagen XXII chemicals. When the collagen XXII protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of collagen XXII without abolishing or substantially altering a collagen XXII activity. Preferably the alteration does not substantially alter the collagen XXII activity, e.g., the activity is at least 20%, 40%, 60%, 70% or 80% of wild-type. An "essential" amino acid residue is a residue that, when altered from the wild-type sequence of collagen XXII, results in abolishing a collagen XXII activity such that less than 20% of the wild-type activity is present. For example, conserved amino acid residues in collagen XXII are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a collagen XXII protein is preferably replaced with another amino acid residue from the same side chain family. Alternatively, in another embodiment, mutations can be introduced randomly along all or part of a collagen XXII coding sequence, such as by saturation mutagenesis, and the resultant mutants can be screened for collagen XXII biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a collagen XXII protein includes a fragment of a collagen XXII protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a collagen XXII molecule and a non-collagen XXII molecule or between a first collagen XXII molecule and a second and/or third collagen XXII molecule (e.g., a dimmer or trimer interaction). Biologically active portions of a collagen XXII protein include peptides comprising amino acid sequences sufficiently homologous to or derived from the amino acid sequence of the collagen XXII protein, e.g., the amino acid sequence shown in SEQ ID NO:2, which include less amino acids than the full length collagen XXII proteins, and exhibit at least one activity of a collagen XXII protein. Typically, biologically active portions comprise a domain or motif with at least one activity of the collagen XXII protein, e.g., triple helix formation or fibril formation. A biologically active portion of a collagen XXII protein can be a polypeptide which is, for example, 10, 25, 50, 100, 200 or more amino acids in length. Biologically active portions of a collagen XXII protein can be used as targets for developing agents which modulate a collagen XXII mediated activity, e.g., tensile strength.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403–10. BLAST nucleotide searches can be performed with the NBLAST program, score=100, wordlength=12 to obtain nucleotide sequences homologous to collagen XXII nucleic acid molecules of the invention. BLAST protein searches can be performed with the XBLAST program, score=50, wordlength=3 to obtain amino acid sequences homologous to collagen XXII protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See www.ncbi.nlm.nih.gov.

Particularly preferred collagen XXII polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a collagen XXII polypeptide described herein, e.g., a full-length collagen XXII protein or a fragment thereof, e.g., a biologically active portion of collagen XXII protein. Also included is a nucleic acid fragment suitable for use as a hybridization probe, which can be used, e.g., to identify a nucleic acid molecule encoding a polypeptide of the invention, collagen XXII mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of these nucleotide sequences. In one embodiment, the nucleic acid molecule includes sequences encoding the human collagen XXII protein (i.e., "the coding region" of SEQ ID NO:1, as shown in SEQ ID NO:3, and alternatively spliced variants thereof), as well as 5' untranslated sequences. Alternatively, the nucleic acid molecule can include only the coding region of SEQ ID NO:1 (e.g., SEQ ID NO:3 or an alternatively spliced variant thereof) and, e.g., no flanking sequences which normally accompany the subject sequence.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3, such that it can hybridize (e.g., under a stringency condition described herein) to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

Collagen XXII Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a collagen XXII protein, e.g., an immunogenic or biologically active portion of a collagen XXII protein. A fragment can comprise those nucleotides of SEQ ID NO:1, which encode a helix forming domain of human collagen XXII. The nucleotide sequence determined from the cloning of the collagen XXII gene allows for the generation of probes and primers designed for use in identifying and/or cloning other collagen XXII family members, or fragments thereof, as well as collagen XXII homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50 amino acids in length. Fragments also include nucleic acid sequences corresponding to specific amino acid sequences described above or fragments thereof. Nucleic acid fragments should not be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a collagen XXII nucleic acid fragment can include a sequence corresponding to a core helical domain or a non-helical interruption.

Collagen XXII probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3. Preferably, an oligonucleotide is less than about 200, 150, 120, or 100 nucleotides in length.

In one embodiment, the probe or primer is attached to a solid support, e.g., a solid support described herein.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO:2. The reverse primer can anneal to the ultimate codon, e.g., the codon immediately before the stop codon. In a preferred embodiment, the annealing temperatures of the forward and reverse primers differ by no more than 5, 4, 3, or 2° C.

In a preferred embodiment the nucleic acid is a probe which is at least 10, 12, 15, 18, 20 and less than 200, more preferably less than 100, or less than 50, nucleotides in length. It should be identical, or differ by 1, or 2, or less than 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a predicted signal peptide, from about amino acid 1–27 of SEQ ID NO:2; a core helical domain rich in G-X-Y repeats from about amino acid 1479–1603 of SEQ ID NO:2; or any of six non-helical interruptions of the core helical domain at about amino acids 853–864, 1004–1024 (present in alternatively spliced variant), 1097–1119, 1457–1495, 1550–1552, and 1572–1575 of SEQ ID NO:2

In another embodiment a set of primers is provided, e.g., primers suitable for use in a PCR, which can be used to amplify a selected region of a collagen XXII sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a predicted signal peptide, from about amino acid 1–27 of SEQ ID NO:2; a core helical domain rich in G-X-Y repeats from about amino acid 1479–1603 of SEQ ID NO:2; or any of six non-helical interruptions of the core helical domain at about amino acids 853–864, 1004–1024 (present in alternatively spliced variant), 1097–1119, 1457–1495, 1550–1552, and 1572–1575 of SEQ ID NO:2

A nucleic acid fragment can encode an epitope bearing region of a polypeptide described herein.

A nucleic acid fragment encoding a "biologically active portion of a collagen XXII polypeptide" can be prepared by isolating a portion of the nucleotide sequence of SEQ ID NO:1 or 3, which encodes a polypeptide having a collagen XXII biological activity (e.g., the biological activities of the collagen XXII proteins are described herein), expressing the encoded portion of the collagen XXII protein (e.g., by recombinant expression in vitro) and assessing the activity of the encoded portion of the collagen XXII protein. For example, a nucleic acid fragment encoding a biologically active portion of collagen XXII includes a core helical domain, e.g., amino acid residues about 1479–1606 of SEQ ID NO:2. A nucleic acid fragment encoding a biologically active portion of a collagen XXII polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:1, or SEQ ID NO:3.

Collagen XXII Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same collagen XXII proteins as those encoded by the nucleotide sequence disclosed herein). In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. The encoded protein can differ by no more than 5, 4, 3, 2, or 1 amino acid. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1 or 3, e.g., as follows: by at least one but less than 10, 20, 30, or 40 nucleotides; at least one but less than 1%, 5%, 10% or 20% of the nucleotides in the subject nucleic acid. The nucleic acid can differ by no more than 5, 4, 3, 2, or 1 nucleotide. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under a stringency condition described herein, to the nucleotide sequence shown in SEQ ID NO 2 or a fragment of the sequence. Nucleic acid molecules corresponding to orthologs, homologs, and allelic variants of the collagen XXII cDNAs of the invention can further be isolated by mapping to the same chromosome or locus as the collagen XXII gene.

Preferred variants include those that are correlated with triple helix forming activity, Allelic variants of collagen XXII, e.g., human collagen XXII, include both functional and non-functional proteins. Functional allelic variants are naturally occurring amino acid sequence variants of the collagen XXII protein within a population that maintain the ability to form a trimeric triple helix. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the collagen XXII, e.g., human collagen XXII, protein within a population that do not have the ability to form a trimeric triple helix. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other collagen XXII family members and, thus, which have a nucleotide sequence which differs from the collagen XXII sequences of SEQ ID NO:1 or SEQ ID NO:3 are intended to be within the scope of the invention.

Antisense Nucleic Acid Molecules, Ribozymes and Modified Collagen XXII Nucleic Acid Molecules In another aspect, the invention features, an isolated nucleic acid molecule which is antisense to collagen XXII. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire collagen XXII coding strand, or to only a portion thereof (e.g., the coding region of human collagen XXII corresponding to SEQ ID NO:3). In another embodiment, the antisense nucleic acid molecule is antisense to a "noncoding region" of the coding strand of a nucleotide sequence encoding collagen XXII (e.g., the 5' and 3' untranslated regions).

An antisense nucleic acid can be designed such that it is complementary to the entire coding region of collagen XXII mRNA, but more preferably is an oligonucleotide which is antisense to only a portion of the coding or noncoding region of collagen XXII mRNA. For example, the antisense oligonucleotide can be complementary to the region surrounding the translation start site of collagen XXII mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a collagen XXII protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. A ribozyme having specificity for a collagen XXII-encoding nucleic acid can include one or more sequences complementary to the nucleotide sequence of a collagen XXII cDNA disclosed herein (i.e., SEQ ID NO:1 or SEQ ID NO:3), and a sequence having known catalytic sequence responsible for mRNA cleavage (see U.S. Pat. No. 5,093,246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a collagen XXII-encoding mRNA. See, e.g., Cech et al. U.S. Pat. No. 4,987,071; and Cech et al. U.S. Pat. No. 5,116,742. Alternatively, collagen XXII mRNA can be used to select a catalytic RNA having a specific ribonuclease activity from a pool of RNA molecules. See, e.g., Bartel, D. and Szostak, J. W. (1993) *Science* 261:1411–1418.

Collagen XXII gene expression can be inhibited by targeting nucleotide sequences complementary to the regulatory region of the collagen XXII (e.g., the collagen XXII promoter and/or enhancers) to form triple helical structures that prevent transcription of the collagen XXII gene in target cells. See generally, Helene, C. (1991) *Anticancer Drug Des.* 6:569–84; Helene, C. i (1992) *Ann. N.Y. Acad. Sci.* 660: 27–36; and Maher, L. J. (1992) *Bioassays* 14:807–15. The potential sequences that can be targeted for triple helix formation can be increased by creating a so-called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A collagen XXII nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40–44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670–675.

PNAs of collagen XXII nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of collagen XXII nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a collagen XXII nucleic acid of the invention, two complementary regions one having a fluorophore and one a quencher such that the molecular beacon is useful for quantitating the presence of the collagen XXII nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated Collagen XXII Polypeptides

In another aspect, the invention features, an isolated collagen XXII protein, or fragment, e.g., a biologically active portion, for use as immunogens or antigens to raise or test (or more generally to bind) anti-collagen XXII antibodies. collagen XXII protein can be isolated from cells or tissue sources using standard protein purification techniques. collagen XXII protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a collagen XXII polypeptide has one or more of the following characteristics:

(i) it has the ability to form a helix;

(ii) it has the ability to form a triple helix consisting of three collagen XXII polypeptide chains;

(iii) it has the ability to form higher order collagen XXII fibrils and/or fibers;

(iv) it has the ability to form at least 1, preferably between 3 and 10 non-helical interruptions or domains within the core helical domain;

(v) it provides tensile strength and/or flexibility to tissue boundaries, e.g., muscle-connective tissue boundaries;

(vi) it can provide form to a tissue, e.g., during growth and/or development, (vii) it can separate or anchor cell layers or tissue, e.g., at muscle-tissue junctions, dermal-epidermal junctions, basement membranes that separate epithelial and mesenchymal structures;

(viii) it can provide a filtration barrier between tissues;

(ix) it can provide transparency, e.g., in the eye;

(x) it is recognized by an R34 antibody described herein;

(xi) it has a molecular weight, e.g., a deduced molecular weight, preferably ignoring any contribution of post translational modifications, amino acid composition or other physical characteristic of SEQ ID NO:2;

(xii) it has an overall sequence similarity of at least 50%, preferably at least 60%, more preferably at least 70, 80, 90, or 95%, with a polypeptide a of SEQ ID NO:2 or an alternatively spliced variant thereof;

(xiii) it can be found in muscle-connective tissue boundaries, in joints, in basement membranes;

(xiv) it has a core helical domain which is preferably about 70%, 80%, 90% or 95% with amino acid residues about 1479–1606 of SEQ ID NO:2;

In a preferred embodiment the collagen XXII protein, or fragment thereof, differs from the corresponding sequence in SEQ ID:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the core helical domain. In another preferred embodiment one or more differences are in the core helical domain or in the non-helical interruption domains.

Other embodiments include a protein that contain one or more changes in amino acid sequence, e.g., a change in an amino acid residue which is not essential for activity. Such collagen XXII proteins differ in amino acid sequence from SEQ ID NO:2, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:2 or an alternatively spliced variant thereof described herein.

In one embodiment, a biologically active portion of a collagen XXII protein includes a core helical domain and at least one non-helical interruption. Moreover, other biologically active portions, in which other regions of the protein are deleted, can be prepared by recombinant techniques and evaluated for one or more of the functional activities of a native collagen XXII protein.

In a preferred embodiment, the collagen XXII protein has an amino acid sequence shown in SEQ ID NO:2. In other embodiments, the collagen XXII protein is substantially identical to SEQ ID NO:2. In yet another embodiment, the collagen XXII protein is substantially identical to SEQ ID NO:2 and retains the functional activity of the protein of SEQ ID NO:2, as described in detail in the subsections above.

Collagen XXII Chimeric or Fusion Proteins

In another aspect, the invention provides collagen XXII chimeric or fusion proteins. As used herein, a collagen XXII "chimeric protein" or "fusion protein" includes a collagen XXII polypeptide linked to a non-collagen XXII polypeptide. A "non-collagen XXII polypeptide" refers to a polypeptide having an amino acid sequence corresponding to a protein which is not substantially homologous to the collagen XXII protein, e.g., a protein which is different from the collagen XXII protein and which is derived from the same or a different organism. The collagen XXII polypeptide of the fusion protein can correspond to all or a portion e.g., a fragment described herein of a collagen XXII amino acid sequence. In a preferred embodiment, a collagen XXII fusion protein includes at least one (or two) biologically active portion of a collagen XXII protein. The non-collagen XXII polypeptide can be fused to the N-terminus or C-terminus of the collagen XXII polypeptide.

The fusion protein can include a moiety which has a high affinity for a ligand. For example, the fusion protein can be a GST-collagen XXII fusion protein in which the collagen XXII sequences are fused to the C-terminus of the GST sequences. Such fusion proteins can facilitate the purification of recombinant collagen XXII. Alternatively, the fusion protein can be a collagen XXII protein containing a heterologous signal sequence at its N-terminus. In certain host cells (e.g., mammalian host cells), expression and/or secretion of collagen XXII can be increased through use of a heterologous signal sequence.

Fusion proteins can include all or a part of a serum protein, e.g., an IgG constant region, or human serum albumin.

The collagen XXII fusion proteins of the invention can be incorporated into pharmaceutical compositions and administered to a subject in vivo. The collagen XXII fusion proteins can be used to affect the bioavailability of a collagen XXII substrate. collagen XXII fusion proteins may be useful therapeutically for the treatment of disorders caused by, for example, (i) aberrant modification or mutation of a gene encoding a collagen XXII protein; (ii) misregulation of the collagen XXII gene; and (iii) aberrant post-translational modification of a collagen XXII protein.

Moreover, the collagen XXII-fusion proteins of the invention can be used as immunogens to produce anti-collagen XXII antibodies in a subject, to purify collagen XXII ligands and in screening assays to identify molecules which inhibit the interaction of collagen XXII with a collagen XXII substrate.

Expression vectors are commercially available that already encode a fusion moiety (e.g., a GST polypeptide). A collagen XXII-encoding nucleic acid can be cloned into such an expression vector such that the fusion moiety is linked in-frame to the collagen XXII protein.

Variants of Collagen XXII Proteins

In another aspect, the invention also features a variant of a collagen XXII polypeptide, e.g., which functions as an agonist (mimetics) or as an antagonist. Variants of the collagen XXII proteins can be generated by mutagenesis, e.g., discrete point mutation, the insertion or deletion of sequences or the truncation of a collagen XXII protein. An agonist of the collagen XXII proteins can retain substantially the same, or a subset, of the biological activities of the naturally occurring form of a collagen XXII protein. An antagonist of a collagen XXII protein can inhibit one or more of the activities of the naturally occurring form of the collagen XXII protein by, for example, competitively modulating a collagen XXII-mediated activity of a collagen XXII protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the collagen XXII protein.

Variants of a collagen XXII protein can be identified by screening combinatorial libraries of mutants, e.g., truncation mutants, of a collagen XXII protein for agonist or antagonist activity.

Libraries of fragments e.g., N terminal, C terminal, or internal fragments, of a collagen XXII protein coding sequence can be used to generate a variegated population of fragments for screening and subsequent selection of variants of a collagen XXII protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of collagen XXII proteins. Recursive ensemble mutagenesis (REM), a new technique which enhances the frequency of functional mutants in the libraries, can be used in combination with the screening assays to identify collagen XXII variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated collagen XXII library. For example, a library of expression vectors can be transfected into a cell line, e.g., a cell line, which ordinarily responds to collagen XXII in a substrate-dependent manner. The transfected cells are then contacted with collagen XXII and the effect of the expression of the mutant on signaling by the collagen XXII substrate can be detected, e.g., by measuring collagen triple helix formation or collagenase sensitivity. Plasmid DNA can then be recovered from the cells which score for inhibition, or alternatively, potentiation of signaling by the collagen XXII substrate, and the individual clones further characterized.

In another aspect, the invention features a method of making a collagen XXII polypeptide, e.g., a peptide having a non-wild type activity, e.g., an antagonist, agonist, or super agonist of a naturally occurring collagen XXII polypeptide, e.g., a naturally occurring collagen XXII polypeptide. The method includes: altering the sequence of a collagen XXII polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a collagen XXII polypeptide a biological activity of a naturally occurring collagen XXII polypeptide. The method includes: altering the sequence, e.g., by substitution or deletion of one or more residues, of a collagen XXII polypeptide, e.g., altering the sequence of a non-conserved region, or a domain or residue described herein, and testing the altered polypeptide for the desired activity.

Anti-Collagen XXII Antibodies

In another aspect, the invention provides an anti-collagen XXII antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91–3242, and Chothia, C. et al. (1987) J. Mol. Biol. 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-collagen XXII antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., collagen XXII polypeptide or fragment thereof. Examples of antigen-binding fragments of the anti-collagen XXII antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-collagen XXII antibody can be a polyclonal or a monoclonal antibody. In other embodiments, the antibody can be recombinantly produced, e.g., produced by phage display or by combinatorial methods.

Phage display and combinatorial methods for generating anti-collagen XXII antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J.* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982, the contents of all of which are incorporated by reference herein).

In one embodiment, the anti-collagen XXII antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Bruggeman et al. 1991 *Eur J Immunol* 21:1323–1326).

An anti-collagen XXII antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041–1043); Liu et al. (1987) PNAS 84:3439–3443; Liu et al., 1987, J. Immunol. 139:3521–3526; Sun et al. (1987) PNAS 84:214–218; Nishimura et al., 1987, Canc. Res. 47:999–1005; Wood et al. (1985) Nature 314:446–449; and Shaw et al., 1988, J. Natl Cancer Inst. 80:1553–1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a collagen XXII or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, Science 229:1202–1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a collagen XXII polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552–525; Verhoeyan et al. 1988 Science 239:1534; Beidler et al. 1988 J. Immunol. 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585, 089, the contents of which are hereby incorporated by reference. Other techniques for humanizing antibodies are described in Padlan et al. EP 519596 A1, published on Dec. 23, 1992.

A full-length collagen XXII protein or, antigenic peptide fragment of collagen XXII can be used as an immunogen or can be used to identify anti-collagen XXII antibodies made with other immunogens, e.g., cells, membrane preparations, and the like. The antigenic peptide of collagen XXII should include at least 8 amino acid residues of the amino acid sequence shown in SEQ ID NO:2 and encompasses an epitope of collagen XXII. Preferably, the antigenic peptide includes at least 10 amino acid residues, more preferably at least 15 amino acid residues, even more preferably at least 20 amino acid residues, and most preferably at least 30 amino acid residues.

Antibodies reactive with, or specific for, any of these regions, or other regions or domains described herein are provided.

Antibodies which bind only native collagen XXII protein, only denatured or otherwise non-native collagen XXII protein, or which bind both, are with in the invention. Antibodies with linear or conformational epitopes are within the invention. Conformational epitopes can sometimes be identified by identifying antibodies which bind to native but not denatured collagen XXII protein.

Preferred epitopes encompassed by the antigenic peptide are regions of collagen XXII are located on the surface of the protein, e.g., hydrophilic regions, as well as regions with high antigenicity. For example, an Emini surface probability analysis of the human collagen XXII protein sequence can be used to indicate the regions that have a particularly high probability of being localized to the surface of the collagen XXII protein and are thus likely to constitute surface residues useful for targeting antibody production.

The anti-collagen XXII antibody can be a single chain antibody. A single-chain antibody (scFV) may be engineered (see, for example, Colcher, D. et al. (1999) Ann N Y Acad Sci 880:263–80; and Reiter, Y. (1996) Clin Cancer Res 2:245–52). The single chain antibody can be dimerized or multimerized to generate multivalent antibodies having specificities for different epitopes of the same target collagen XXII protein.

In a preferred embodiment the antibody has effector function and/or can fix complement. In other embodiments the antibody does not recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

In a preferred embodiment, an anti-collagen XXII antibody alters (e.g., increases or decreases) a collagen XXII activity, e.g., triple helix forming activity or tensile strength providing activity, of a collagen XXII polypeptide.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-collagen XXII antibody (e.g., monoclonal antibody) can be used to isolate collagen XXII by standard techniques, such as affinity chromatography or immunoprecipitation. Moreover, an anti-collagen XXII antibody can be used to detect collagen XXII protein (e.g., in a cellular lysate or cell supernatant) in order to evaluate the abundance and pattern of expression of the protein. Anti-collagen XXII antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acid which encodes an anti-collagen XXII antibody, e.g., an anti-collagen XXII antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-collagen XXII antibody, e.g., and antibody described herein, and method of using said cells to make a collagen XXII antibody.

In a preferred embodiment, the antibody is R34 antibody described herein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a collagen XXII nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., collagen XXII proteins, mutant forms of collagen XXII proteins, fusion proteins, and the like).

The recombinant expression vectors of the invention can be designed for expression of collagen XXII proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in collagen XXII activity assays, (e.g., direct assays or competitive assays described in detail below), or to generate antibodies specific for collagen XXII proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The collagen XXII expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a collagen XXII nucleic acid molecule within a recombinant expression vector or a collagen XXII nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a collagen XXII protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *CellI* 23:175–182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a collagen XXII protein. Accordingly, the invention further provides methods for producing a collagen XXII protein using the host cells of the invention. In one embodiment, the method includes culturing the host cell of the invention (into which a recombinant expression vector encoding a collagen XXII protein has been introduced) in a suitable medium such that a collagen XXII protein is produced. In another embodiment, the method further includes isolating a collagen XXII protein from the medium or the host cell.

In another aspect, the invention features, a cell or purified preparation of cells which include a collagen XXII transgene, or which otherwise misexpress collagen XXII. The cell preparation can consist of human or non-human cells, e.g., rodent cells, e.g., mouse or rat cells, rabbit cells, or pig cells. In preferred embodiments, the cell or cells include a collagen XXII transgene, e.g., a heterologous form of a collagen XXII, e.g., a gene derived from humans (in the case of a non-human cell). The collagen XXII transgene can be misexpressed, e.g., overexpressed or underexpressed. In other preferred embodiments, the cell or cells include a gene that mis-expresses an endogenous collagen XXII, e.g., a gene the expression of which is disrupted, e.g., a knockout. Such cells can serve as a model for studying disorders that are related to mutated or mis-expressed collagen XXII alleles or for use in drug screening.

In another aspect, the invention features, a human cell, a cartilage or connective tissue cell, transformed with nucleic acid which encodes a subject collagen XXII polypeptide.

Also provided are cells, preferably human cells, e.g., muscle or connective tissue or fibroblast cells, in which an endogenous collagen XXII is under the control of a regulatory sequence that does not normally control the expression of the endogenous collagen XXII gene. The expression characteristics of an endogenous gene within a cell, e.g., a cell line or microorganism, can be modified by inserting a heterologous DNA regulatory element into the genome of the cell such that the inserted regulatory element is operably linked to the endogenous collagen XXII gene. For example, an endogenous collagen XXII gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a collagen XXII polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of collagen XXII polypeptide can be regulated in the subject by administering an agent (e.g., a steroid hormone) to the subject. In another preferred embodiment, the implanted recombinant cells express and secrete an antibody specific for a collagen XXII polypeptide. The antibody can be any antibody or any antibody derivative described herein.

Transgenic Animals

The invention provides non-human transgenic animals. Such animals are useful for studying the function and/or activity of a collagen XXII protein and for identifying and/or evaluating modulators of collagen XXII activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous collagen XXII gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a collagen XXII protein to particular cells. A transgenic founder animal can be identified based upon the presence of a collagen XXII transgene in its genome and/or expression of collagen XXII mRNA in tissues or cells of the animals. A transgenic founder animal can then be used to breed additional animals carrying the transgene. Moreover, transgenic animals carrying a transgene encoding a collagen XXII protein can further be bred to other transgenic animals carrying other transgenes.

collagen XXII proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); c) methods of treatment (e.g., therapeutic and prophylactic); and d) biomaterials.

The isolated nucleic acid molecules of the invention can be used, for example, to express a collagen XXII protein (e.g., via a recombinant expression vector in a host cell in gene therapy applications), to detect a collagen XXII mRNA (e.g., in a biological sample) or a genetic alteration in a collagen XXII gene, and to modulate collagen XXII activity, as described further below. The collagen XXII proteins can be used to treat disorders characterized by insufficient or excessive production of a collagen XXII substrate or production of collagen XXII inhibitors. In addition, the collagen XXII proteins can be used to screen for naturally occurring collagen XXII substrates, to screen for drugs or compounds which modulate collagen XXII activity, as well as to treat disorders characterized by insufficient or excessive production of collagen XXII protein or production of collagen XXII protein forms which have decreased, aberrant or unwanted activity compared to collagen XXII wild type protein. Moreover, the anti-collagen XXII antibodies of the invention can be used to detect and isolate collagen XXII proteins, regulate the bioavailability of collagen XXII proteins, and modulate collagen XXII activity.

A method of evaluating a compound for the ability to interact with, e.g., bind, a subject collagen XXII polypeptide is provided. The method includes: contacting the compound with the subject collagen XXII polypeptide; and evaluating ability of the compound to interact with, e.g., to bind or form a complex with the subject collagen XXII polypeptide. This method can be performed in vitro, e.g., in a cell free system, or in vivo, e.g., in a two-hybrid interaction trap assay. This method can be used to identify naturally occurring molecules that interact with subject collagen XXII polypeptide. It can also be used to find natural or synthetic inhibitors of subject collagen XXII polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to collagen XXII proteins, have a stimulatory or inhibitory effect on, for example, collagen XXII expression or collagen XXII activity, or have a stimulatory or inhibitory effect on, for example, the expression or activity of a collagen XXII substrate. Compounds thus identified can be used to modulate the activity of target gene products (e.g., collagen XXII genes) in a therapeutic protocol, to elaborate the biological function of the target gene product, or to identify compounds that disrupt normal target gene interactions.

In one embodiment, the invention provides assays for screening candidate or test compounds which are substrates of a collagen XXII protein or polypeptide or a biologically active portion thereof. In another embodiment, the invention provides assays for screening candidate or test compounds that bind to or modulate an activity of a collagen XXII protein or polypeptide or a biologically active portion thereof.

In one embodiment, an activity of a collagen XXII protein can be assayed as follows. Triple helix formation can be assayed by: incubating type XXII collagen polypeptides together under conditions that promote helix formation; separating the incubation mixture and a control mixture on a non-reducing PAGE gel; and comparing the incubation mixture to the control mixture. The mobility of collagen XXII dimers and trimers (detected by protein staining or antibody binding) will be distinguishable from the mobility of uncomplexed collagen XXII polypeptide chains on a PAGE gel. Collagen expression can be assayed by sensitivity to collagenase by methods known in the art.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a collagen XXII protein or biologically active portion thereof is contacted with a test compound, and the ability of the test compound to modulate collagen XXII activity is determined. Determining the ability of the test compound to modulate collagen XXII activity can be accomplished by monitoring, for example, triple helix formation The cell, for example, can be of mammalian origin, e.g., human.

The ability of the test compound to modulate collagen XXII binding to a compound, e.g., a collagen XXII substrate, or to bind to collagen XXII can also be evaluated. This can be accomplished, for example, by coupling the compound, e.g., the substrate, with a radioisotope or enzymatic label such that binding of the compound, e.g., the substrate, to collagen XXII can be determined by detecting the labeled compound, e.g., substrate, in a complex. Alternatively, collagen XXII could be coupled with a radioisotope or enzymatic label to monitor the ability of a test compound to modulate collagen XXII binding to a collagen XXII substrate in a complex. For example, compounds (e.g., collagen XXII substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a collagen XXII substrate) to interact with collagen XXII with or without the labeling of any of the interactants can be evaluated. For example, a microphysiometer can be used to detect the interaction of a compound with collagen XXII without the labeling of either the compound or the collagen XXII. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and collagen XXII.

In yet another embodiment, a cell-free assay is provided in which a collagen XXII protein or biologically active portion thereof is contacted with a test compound and the ability of the test compound to bind to the collagen XXII protein or biologically active portion thereof is evaluated. Preferred biologically active portions of the collagen XXII proteins to be used in assays of the present invention include fragments which participate in interactions with non-collagen XXII molecules, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the collagen XXII protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995)

Curr. Opin. Struct. Biol. 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either collagen XXII, an anti-collagen XXII antibody or its target molecule to facilitate separation of complexed from uncomplexed forms of one or both of the proteins, as well as to accommodate automation of the assay. Binding of a test compound to a collagen XXII protein, or interaction of a collagen XXII protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/collagen XXII fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or collagen XXII protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of collagen XXII binding or activity determined using standard techniques.

Other techniques for immobilizing either a collagen XXII protein or a target molecule on matrices include using conjugation of biotin and streptavidin. Biotinylated collagen XXII protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with collagen XXII protein or target molecules but which do not interfere with binding of the collagen XXII protein to its target molecule. Such antibodies can be derivatized to the wells of the plate, and unbound target or collagen XXII protein trapped in the wells by antibody conjugation. Methods for detecting such complexes, in addition to those described above for the GST-immobilized complexes, include immunodetection of complexes using antibodies reactive with the collagen XXII protein or target molecule, as well as enzyme-linked assays which rely on detecting an enzymatic activity associated with the collagen XXII protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11: 141–8; Hage, D. S., and Tweed, S. A. (1997) *J Chromatogr B Biomed Sci Appl*. 699:499–525). Further, fluorescence energy transfer may also be conveniently utilized, as described herein, to detect binding without further purification of the complex from solution.

In a preferred embodiment, the assay includes contacting the collagen XXII protein or biologically active portion thereof with a known compound which binds collagen XXII to form an assay mixture, contacting the assay mixture with a test compound, and determining the ability of the test compound to interact with a collagen XXII protein, wherein determining the ability of the test compound to interact with a collagen XXII protein includes determining the ability of the test compound to preferentially bind to collagen XXII or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the collagen XXII genes herein identified. In an alternative embodiment, the invention provides methods for determining the ability of the test compound to modulate the activity of a collagen XXII protein through modulation of the activity of a downstream effector of a collagen XXII target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the collagen XXII proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with collagen XXII ("collagen XXII-binding proteins" or "collagen XXII-bp") and are involved in collagen XXII activity. Such collagen XXII-bps can be activators or inhibitors of signals by the collagen XXII proteins or collagen XXII targets as, for example, downstream elements of a collagen XXII-mediated signaling pathway.

The two-hybrid system is based on the modular nature of most transcription factors, which consist of separable DNA-binding and activation domains. Briefly, the assay utilizes two different DNA constructs. In one construct, the gene that codes for a collagen XXII protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: collagen XXII protein can be the fused to the activator domain.) If the "bait" and the "prey" proteins are able to interact, in vivo, forming a collagen XXII-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the collagen XXII protein.

In another embodiment, modulators of collagen XXII expression are identified. For example, a cell or cell free mixture is contacted with a candidate compound and the expression of collagen XXII mRNA or protein evaluated relative to the level of expression of collagen XXII mRNA or protein in the absence of the candidate compound. When expression of collagen XXII mRNA or protein is greater in the presence of the candidate compound than in its absence, the candidate compound is identified as a stimulator of collagen XXII mRNA or protein expression. Alternatively, when expression of collagen XXII mRNA or protein is less (statistically significantly less) in the presence of the candidate compound than in its absence, the candidate compound is identified as an inhibitor of collagen XXII mRNA or protein expression. The level of collagen XXII mRNA or protein expression can be determined by methods described herein for detecting collagen XXII mRNA or protein.

In another aspect, the invention pertains to a combination of two or more of the assays described herein. For example, a modulating agent can be identified using a cell-based or a cell free assay, and the ability of the agent to modulate the activity of a collagen XXII protein can be confirmed in vivo, e.g., in an animal such as an animal model for a connective tissue or joint disorder.

This invention further pertains to novel agents identified by the above-described screening assays. Accordingly, it is within the scope of this invention to further use an agent identified as described herein (e.g., a collagen XXII modulating agent, an antisense collagen XXII nucleic acid molecule, a collagen XXII-specific antibody, or a collagen XXII-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate collagen XXII with a disease; (ii) identify an individual from a minute biological sample (tissue typing); and (iii) aid in forensic identification of a biological sample. These applications are described in the subsections below.

Chromosome Mapping

The collagen XXII nucleotide sequences or portions thereof can be used to map the location of the collagen XXII genes on a chromosome. This process is called chromosome mapping. Chromosome mapping is useful in correlating the collagen XXII sequences with genes associated with disease.

Briefly, collagen XXII genes can be mapped to chromosomes by preparing PCR primers (preferably 15–25 bp in length) from the collagen XXII nucleotide sequences. These primers can then be used for PCR screening of somatic cell hybrids containing individual human chromosomes. Only those hybrids containing the human gene corresponding to the collagen XXII sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map collagen XXII to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the collagen XXII gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing collagen XXII sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the collagen XXII nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from collagen XXII nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial Collagen XXII Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The collagen XXII nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such collagen XXII probes can be used to identify tissue by species and/or by organ type.

In a similar fashion, these reagents, e.g., collagen XXII primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes collagen XXII.

Such disorders include, e.g., a disorder associated with the misexpression of collagen XXII gene; a disorder of the connective tissue system.

The method includes one or more of the following:

detecting, in a tissue of the subject, the presence or absence of a mutation which affects the expression of the collagen XXII gene, or detecting the presence or absence of a mutation in a region which controls the expression of the gene, e.g., a mutation in the 5' control region;

detecting, in a tissue of the subject, the presence or absence of a mutation which alters the structure of the collagen XXII gene;

detecting, in a tissue of the subject, the misexpression of the collagen XXII gene, at the mRNA level, e.g., detecting a non-wild type level of a mRNA;

detecting, in a tissue of the subject, the misexpression of the gene, at the protein level, e.g., detecting a non-wild type level of a collagen XXII polypeptide.

In preferred embodiments the method includes: ascertaining the existence of at least one of: a deletion of one or more nucleotides from the collagen XXII gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the collagen XXII gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the collagen XXII gene; the presence of a non-wild type splicing pattern of a messenger RNA transcript of the gene; or a non-wild type level of collagen XXII.

Methods of the invention can be used prenatally or to determine if a subject's offspring will be at risk for a disorder.

In preferred embodiments the method includes determining the structure of a collagen XXII gene, an abnormal structure being indicative of risk for the disorder.

In preferred embodiments the method includes contacting a sample from the subject with an antibody to the collagen XXII protein or a nucleic acid, which hybridizes specifically with the gene. These and other embodiments are discussed below.

Diagnostic and Prognostic Assays

Diagnostic and prognostic assays of the invention include method for assessing the expression level of collagen XXII molecules and for identifying variations and mutations in the sequence of collagen XXII molecules.

Expression Monitoring and Profiling. The presence, level, or absence of collagen XXII protein or nucleic acid in a biological sample can be evaluated by obtaining a biological sample from a test subject and contacting the biological sample with a compound or an agent capable of detecting collagen XXII protein or nucleic acid (e.g., mRNA, genomic DNA) that encodes collagen XXII protein such that the presence of collagen XXII protein or nucleic acid is detected in the biological sample. The term "biological sample" includes tissues, cells and biological fluids isolated from a subject, as well as tissues, cells and fluids present within a subject. A preferred biological sample is serum. The level of expression of the collagen XXII gene can be measured in a number of ways, including, but not limited to: measuring the mRNA encoded by the collagen XXII genes; measuring the amount of protein encoded by the collagen XXII genes; or measuring the activity of the protein encoded by the collagen XXII genes.

The level of mRNA corresponding to the collagen XXII gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length collagen XXII nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to collagen XXII mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the collagen XXII genes.

The level of mRNA in a sample that is encoded by one of collagen XXII can be evaluated with nucleic acid amplification, e.g., by rtPCR (Mullis (1987) U.S. Pat. No. 4,683, 202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the collagen XXII gene being analyzed.

In another embodiment, the methods further contacting a control sample with a compound or agent capable of detecting collagen XXII mRNA, or genomic DNA, and comparing the presence of collagen XXII mRNA or genomic DNA in the control sample with the presence of collagen XXII mRNA or genomic DNA in the test sample. In still another embodiment, serial analysis of gene expression, as described in U.S. Pat. No. 5,695,937, is used to detect collagen XXII transcript levels.

A variety of methods can be used to determine the level of protein encoded by collagen XXII. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect collagen XXII protein in a biological sample in vitro as well as in vivo. In vitro techniques for detection of collagen XXII protein include enzyme linked immunosorbent assays (ELISAs), immunoprecipitations, immunofluorescence, enzyme immunoassay (EIA), radioimmunoassay (RIA), and Western blot analysis. In vivo techniques for detection of collagen XXII protein include introducing into a subject a labeled anti-collagen XXII antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-collagen XXII antibody positioned on an antibody array (as described below). The sample can be detected, e.g., with avidin coupled to a fluorescent label.

In another embodiment, the methods further include contacting the control sample with a compound or agent capable of detecting collagen XXII protein, and comparing the presence of collagen XXII protein in the control sample with the presence of collagen XXII protein in the test sample.

The invention also includes kits for detecting the presence of collagen XXII in a biological sample. For example, the kit can include a compound or agent capable of detecting collagen XXII protein or mRNA in a biological sample; and a standard. The compound or agent can be packaged in a suitable container. The kit can further comprise instructions for using the kit to detect collagen XXII protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted collagen XXII expression or activity. As used herein, the term "unwanted" includes an unwanted phenomenon involved in a biological response such as connective tissue formation and maintenace.

In one embodiment, a disease or disorder associated with aberrant or unwanted collagen XXII expression or activity is identified. A test sample is obtained from a subject and collagen XXII protein or nucleic acid (e.g., mRNA or genomic DNA) is evaluated, wherein the level, e.g., the presence or absence, of collagen XXII protein or nucleic acid is diagnostic for a subject having or at risk of developing a disease or disorder associated with aberrant or unwanted collagen XXII expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted collagen XXII expression or activity.

In another aspect, the invention features a computer medium having a plurality of digitally encoded data records. Each data record includes a value representing the level of expression of collagen XXII in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than collagen XXII (e.g., other genes associated with a collagen XXII-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of collagen XXII expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a connective tissue disorder in a subject wherein an increase or decrease in collagen XXII expression is an indication that the subject has or is disposed to having a connective tissue disorder The method can be used to monitor a treatment for a connective tissue disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of collagen XXII expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of collagen XXII expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of collagen XXII expression.

Arrays and Uses Thereof

In another aspect, the invention features an array that includes a substrate having a plurality of addresses. At least one address of the plurality includes a capture probe that binds specifically to a collagen XXII molecule (e.g., a collagen XXII nucleic acid or a collagen XXII polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a collagen XXII nucleic acid, e.g., the sense or anti-sense strand. In one preferred embodiment, a subset of addresses of the plurality of addresses has a nucleic acid capture probe for collagen XXII. Each address of the subset can include a capture probe that hybridizes to a different region of a collagen XXII nucleic acid. In another preferred embodiment, addresses of the subset include a capture probe for a collagen XXII nucleic acid. Each address of the subset is unique, overlapping, and complementary to a different variant of collagen XXII (e.g., an allelic variant, or all possible hypothetical variants). The array can be used to sequence collagen XXII by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a collagen XXII polypeptide or fragment thereof. The polypeptide can be a naturally-occurring interaction partner of collagen XXII polypeptide. Preferably, the polypeptide is an antibody, e.g., an antibody described herein (see "Anti-collagen XXII Antibodies," above), such as a monoclonal antibody or a single-chain antibody.

In another aspect, the invention features a method of analyzing the expression of collagen XXII. The method includes providing an array as described above; contacting the array with a sample and detecting binding of a collagen XXII-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of collagen XXII. If a sufficient number of diverse samples is analyzed, clustering (e.g., hierarchical clustering, k-means clustering, Bayesian clustering and the like) can be used to identify other genes which are co-regulated with collagen XXII. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell—cell interactions on collagen XXII expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell—cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a collagen XXII-associated disease or disorder; and processes, such as a cellular transformation associated with a collagen XXII-associated disease or disorder. The method can also evaluate the treatment and/or progression of a collagen XXII-associated disease or disorder The array is also useful for ascertaining differential expression patterns of one or more genes in normal and abnormal cells. This provides a battery of genes (e.g., including collagen XXII) that could serve as a molecular target for diagnosis or therapeutic intervention.

In another aspect, the invention features an array having a plurality of addresses. Each address of the plurality includes a unique polypeptide. At least one address of the plurality has disposed thereon a collagen XXII polypeptide or fragment thereof. Methods of producing polypeptide arrays are described in the art, e.g., in De Wildt et al. (2000). *Nature Biotech.* 18, 989–994; Lueking et al. (1999). *Anal. Biochem.* 270, 103–111; Ge, H. (2000). *Nucleic Acids Res.* 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80, 85, 90, 95 or 99% identical to a collagen XXII polypeptide or fragment thereof. For example, multiple variants of a collagen XXII polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a collagen XXII binding compound, e.g., an antibody in a sample from a subject with specificity for a collagen XXII polypeptide or the presence of a collagen XXII-binding protein or ligand.

The array is also useful for ascertaining the effect of the expression of a gene on the expression of other genes in the same cell or in different cells (e.g., ascertaining the effect of collagen XXII expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express collagen XXII or from a cell or subject in which a collagen XXII mediated response has been elicited, e.g., by contact of the cell with collagen XXII nucleic acid or protein, or administration to the cell or subject collagen XXII nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express collagen XXII (or does not express as highly as in the case of the collagen XXII positive plurality of capture probes) or from a cell or subject which in which a collagen XXII mediated response has not been elicited (or has been elicited to a lesser extent than in the first sample); contacting the array with one or more inquiry probes (which is preferably other than a collagen XXII nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express collagen XXII or from a cell or subject in which a collagen XXII-mediated response has been elicited, e.g., by contact of the cell with collagen XXII nucleic acid or protein, or administration to the cell or subject collagen XXII nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express collagen XXII (or does not express as highly as in the case of the collagen XXII positive plurality of capture probes) or from a cell or subject which in which a collagen XXII mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing collagen XXII, e.g., analyzing structure, function, or relatedness to other nucleic acid or amino acid sequences. The method includes: providing a collagen XXII nucleic acid or amino acid sequence; comparing the collagen XXII sequence with one or more preferably a plurality of sequences from a collection of sequences, e.g., a nucleic acid or protein sequence database; to thereby analyze collagen XXII.

Detection of Variations or Mutations

The methods of the invention can also be used to detect genetic alterations in a collagen XXII gene, thereby determining if a subject with the altered gene is at risk for a disorder characterized by misregulation in collagen XXII protein activity or nucleic acid expression, such as a connective tissue disorder. In preferred embodiments, the methods include detecting, in a sample from the subject, the presence or absence of a genetic alteration characterized by at least one of an alteration affecting the integrity of a gene encoding a collagen XXII-protein, or the mis-expression of the collagen XXII gene. For example, such genetic alterations can be detected by ascertaining the existence of at least one of 1) a deletion of one or more nucleotides from a collagen XXII gene; 2) an addition of one or more nucleotides to a collagen XXII gene; 3) a substitution of one or more nucleotides of a collagen XXII gene, 4) a chromosomal rearrangement of a collagen XXII gene; 5) an alteration in the level of a messenger RNA transcript of a collagen XXII gene, 6) aberrant modification of a collagen XXII gene, such as of the methylation pattern of the genomic DNA, 7) the presence of a non-wild type splicing pattern of a messenger RNA transcript of a collagen XXII gene, 8) a non-wild type level of a collagen XXII-protein, 9) allelic loss of a collagen XXII gene, and 10) inappropriate post-translational modification of a collagen XXII-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the collagen XXII-gene. This method can include the steps of collecting a sample of cells from a subject, isolating nucleic acid (e.g., genomic, mRNA or both) from the sample, contacting the nucleic acid sample with one or more primers which specifically hybridize to a collagen XXII gene under conditions such that hybridization and amplification of the collagen XXII-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a collagen XXII gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in collagen XXII can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a collagen XXII nucleic acid or a putative variant (e.g., allelic variant) thereof. A probe can have one or more mismatches to a region of a collagen XXII nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in collagen XXII can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the collagen XXII gene and detect mutations by comparing the sequence of the sample collagen XXII with the corresponding wild-type (control) sequence. Automated sequencing procedures can be utilized when performing the diagnostic assays ((1995) *Biotechniques* 19:448), including sequencing by mass spectrometry.

Other methods for detecting mutations in the collagen XXII gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl. Acad Sci USA* 85:4397; Saleeba et al. (1992) *Methods Enzymol.* 217: 286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in collagen XXII cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in collagen XXII genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control collagen XXII nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a collagen XXII nucleic acid.

In a preferred embodiment the set includes a first and a second oligonucleotide. The first and second oligonucleotide can hybridize to the same or to different locations of SEQ ID NO:1 or the complement of SEQ ID NO:1. Different locations can be different but overlapping, or non-overlapping on the same strand. The first and second oligonucleotide can hybridize to sites on the same or on different strands.

The set can be useful, e.g., for identifying SNP's, or identifying specific alleles of collagen XXII. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a collagen XXII nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a collagen XXII gene.

Use of Collagen XXII Molecules as Surrogate Markers

The collagen XXII molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the collagen XXII molecules of the invention may be detected, and may be correlated with one or more biological states in vivo. For example, the collagen XXII molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The collagen XXII molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a collagen XXII marker) transcription or expression, the amplified marker may be in a quantity which is more readily detectable than the drug itself. Also, the marker may be more easily detected due to the nature of the marker itself; for example, using the methods described herein, anti-collagen XXII antibodies may be employed in an immune-based detection system for a collagen XXII protein marker, or collagen XXII-specific radiolabeled probes may be used to detect a collagen XXII mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The collagen XXII molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., collagen XXII protein or RNA) for specific tumor markers in a subject, a drug or course of treatment may be selected that is optimized for the treatment of the specific tumor likely to be present in the subject. Similarly, the presence or absence of a specific sequence mutation in collagen XXII DNA may correlate collagen XXII drug response. The use of pharmacogenomic markers therefore permits the application of the most appropriate treatment for each subject without having to administer the therapy.

Pharmaceutical Compositions

The nucleic acid and polypeptides, fragments thereof, as well as anti-collagen XXII antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with, e.g., insufficient, aberrant, or unwanted collagen XXII expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the collagen XXII molecules of the present invention or collagen XXII modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted collagen XXII expression or activity, by administering to the subject a collagen XXII or an agent which modulates collagen XXII expression or at least one collagen XXII activity. Subjects at risk for a disease which is caused or contributed to by aberrant or unwanted collagen XXII expression or activity can be identified by, for example, any or a combination of diagnostic or prognostic assays as described herein. Administration of a prophylactic agent can occur prior to the manifestation of symptoms characteristic of the collagen XXII aberrance, such that a disease or disorder is prevented or, alternatively, delayed in its progression. Depending on the type of collagen XXII aberrance, for example, a collagen XXII, collagen XXII agonist or collagen XXII antagonist agent can be used for treating the subject. The appropriate agent can be determined based on screening assays described herein.

It is possible that some collagen XXII disorders can be caused, at least in part, by an abnormal level of gene product, or by the presence of a gene product exhibiting abnormal activity. As such, the reduction in the level and/or activity of such gene products would bring about the amelioration of disorder symptoms. In addition, the collagen XXII molecules described herein can serve to increase the success of transplants, e.g., transplants of connective tissue, e.g., cartilage, tendon, lens, heart valves, or hair follicles.

As discussed, successful treatment of collagen XXII disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of collagen XXII disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by collagen XXII expression is through the use of aptamer molecules specific for collagen XXII protein. Aptamers are nucleic acid molecules having a tertiary structure which permits them to specifically bind to protein ligands (see, e.g., Osborne, et al. (1997) *Curr. Opin. Chem Biol.* 1: 5–9; and Patel, D. J. (1997) *Curr Opin Chem Biol* 1:32–46). Since nucleic acid molecules may in many cases be more conveniently introduced into target cells than therapeutic protein molecules may be, aptamers offer a method by which collagen XXII protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of collagen XXII disorders. For a description of antibodies, see the Antibody section above.

In circumstances wherein injection of an animal or a human subject with a collagen XXII protein or epitope for stimulating antibody production is harmful to the subject, it is possible to generate an immune response against collagen XXII through the use of anti-idiotypic antibodies (see, for example, Herlyn, D. (1999) *Ann Med* 31:66–78; and Bhattacharya-Chatterjee, M., and Foon, K. A. (1998) *Cancer Treat Res.* 94:51–68). If an anti-idiotypic antibody is introduced into a mammal or human subject, it should stimulate the production of anti-anti-idiotypic antibodies, which should be specific to the collagen XXII protein. Vaccines directed to a disease characterized by collagen XXII expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate collagen XXII disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate collagen XXII activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of collagen XXII can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating collagen XXII expression or activity for therapeutic purposes, e.g., for use in transplants of, e.g., connective tissue, e.g., cartilage, tendon, lens, heart valves, or hair follicles. Accordingly, in an exemplary embodiment, the modulatory method of the invention involves contacting a cell with a collagen XXII or agent that modulates one or more of the activities of collagen XXII protein activity associated with the cell. An agent that modulates collagen XXII protein activity can be an agent as described herein, such as a nucleic acid or a protein, a naturally-occurring target molecule of a collagen XXII protein (e.g., a collagen XXII substrate or receptor), a collagen XXII antibody, a collagen XXII agonist or antagonist, a peptidomimetic of a collagen XXII agonist or antagonist, or other small molecule.

In one embodiment, the agent stimulates one or more collagen XXII activities. Examples of such stimulatory agents include active collagen XXII protein and a nucleic acid molecule encoding collagen XXII. In another embodiment, the agent inhibits one or more collagen XXII activities. Examples of such inhibitory agents include antisense collagen XXII nucleic acid molecules, anti-collagen XXII antibodies, and collagen XXII inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a collagen XXII protein or nucleic acid molecule. In one embodiment, the method involves administering an agent (e.g., an agent identified by a screening assay described herein), or combination of agents that modulates (e.g., up regulates or down regulates) collagen XXII expression or activity. In another embodiment, the method involves administering a collagen XXII protein or nucleic acid molecule as therapy to compensate for reduced, aberrant, or unwanted collagen XXII expression or activity.

Stimulation of collagen XXII activity is desirable in situations in which collagen XXII is abnormally downregulated and/or in which increased collagen XXII activity is likely to have a beneficial effect. For example, stimulation of collagen XXII activity is desirable in situations in which a collagen XXII is downregulated and/or in which increased collagen XXII activity is likely to have a beneficial effect. Likewise, inhibition of collagen XXII activity is desirable in situations in which collagen XXII is abnormally upregulated and/or in which decreased collagen XXII activity is likely to have a beneficial effect.

Pharmacogenomics

The collagen XXII molecules of the present invention, as well as agents, or modulators which have a stimulatory or inhibitory effect on collagen XXII activity (e.g., collagen XXII gene expression) as identified by a screening assay described herein can be administered to individuals to treat (prophylactically or therapeutically) collagen XXII associated, e.g., connective tissue disorders, associated with aberrant or unwanted collagen XXII activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a collagen XXII molecule or collagen XXII modulator as well as tailoring the dosage and/or therapeutic regimen of treatment with a collagen XXII molecule or collagen XXII modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a collagen XXII protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a collagen XXII molecule or collagen XXII modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a collagen XXII molecule or collagen XXII modulator, such as a modulator identified by one of the exemplary screening assays described herein.

The present invention further provides methods for identifying new agents, or combinations, that are based on identifying agents that modulate the activity of one or more of the gene products encoded by one or more of the collagen XXII genes of the present invention, wherein these products may be associated with resistance of the cells to a therapeutic agent. Specifically, the activity of the proteins encoded by the collagen XXII genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a collagen XXII protein can be applied in clinical trials. For example, the effectiveness of an agent determined by a screening assay as described herein to increase collagen XXII gene expression, protein levels, or upregulate collagen XXII activity, can be monitored in clinical trials of subjects exhibiting decreased collagen XXII gene expression, protein levels, or downregulated collagen XXII activity. Alternatively, the effectiveness of an agent determined by a screening assay to decrease collagen XXII gene expression, protein levels, or downregulate collagen XXII activity, can be monitored in clinical trials of subjects exhibiting increased collagen XXII gene expression, protein levels, or upregulated collagen XXII activity. In such clinical trials, the expression or activity of a collagen XXII gene, and preferably, other genes that have been implicated in, for example, a collagen XXII-associated disorder can be used as a "read out" or markers of the phenotype of a particular cell.

Collagen XXII Informatics

The sequence of a collagen XXII molecule is provided in a variety of media to facilitate use thereof. A sequence can be provided as a manufacture, other than an isolated nucleic acid or amino acid molecule, which contains a collagen XXII. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, collagen XXII full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers.

Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing collagen XXII, e.g., analyzing structure, function, or relatedness to one or more other nucleic acid or amino acid sequences. The method includes: providing a collagen XXII nucleic acid or amino acid sequence; comparing the collagen XXII sequence with a second sequence, e.g., one or more preferably a plurality of sequences from a collection of sequences, e.g., a nucleic acid or protein sequence database to thereby analyze collagen XXII. The method can be performed in a machine, e.g., a computer, or manually by a skilled artisan.

The method can include evaluating the sequence identity between a collagen XXII sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a collagen XXII sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a collagen XXII sequence, or record, in machine-readable form; comparing a second sequence to the collagen XXII sequence; thereby analyzing a sequence. Comparison can include comparing to sequences for sequence identity or determining if one sequence is included within the other, e.g., determining if the collagen XXII sequence includes a sequence being compared. In a preferred embodiment the collagen XXII or second sequence is stored on a first computer, e.g., at a first site and the comparison is performed, read, or recorded on a second computer, e.g., at a second site. E.g., the collagen XXII or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a collagen XXII-associated disease or disorder or a pre-disposition to a collagen XXII-associated disease or disorder, wherein the method comprises the steps of determining collagen XXII sequence information associated with the subject and based on the collagen XXII sequence information, determining whether the subject has a collagen XXII-associated disease or disorder or a pre-disposition to a collagen XXII-associated disease or disorder and/or recommending a particular treatment for the disease, disorder or pre-disease condition.

The invention further provides in an electronic system and/or in a network, a method for determining whether a subject has a collagen XXII-associated disease or disorder or a pre-disposition to a disease associated with a collagen XXII wherein the method comprises the steps of determining collagen XXII sequence information associated with the subject, and based on the collagen XXII sequence information, determining whether the subject has a collagen XXII-associated disease or disorder or a pre-disposition to a collagen XXII-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the collagen XXII sequence of the subject to the collagen XXII sequences in the database to thereby determine whether the subject as a collagen XXII-associated disease or disorder, or a pre-disposition for such.

The present invention also provides in a network, a method for determining whether a subject has a collagen XXII associated disease or disorder or a pre-disposition to a collagen XXII-associated disease or disorder associated with collagen XXII, said method comprising the steps of receiving collagen XXII sequence information from the subject and/or information related thereto, receiving phenotypic information associated with the subject, acquiring information from the network corresponding to collagen XXII and/or corresponding to a collagen XXII-associated disease or disorder (e.g., a connective tissue disorder, and based on one or more of the phenotypic information, the collagen XXII information (e.g., sequence information and/or information related thereto), and the acquired information, determining whether the subject has a collagen XXII-associated disease or disorder or a pre-disposition to a collagen XXII-associated disease or disorder. The method may further comprise the step of recommending a particular treatment for the disease, disorder or pre-disease condition.

The present invention also provides a method for determining whether a subject has a collagen XXII-associated disease or disorder or a pre-disposition to a collagen XXII-associated disease or disorder, said method comprising the steps of receiving information related to collagen XXII (e.g., sequence information and/or information related thereto), receiving phenotypic information associated with the subject, acquiring information from the network related to collagen XXII and/or related to a collagen XXII-associated disease or disorder, and based on one or more of the phenotypic information, the collagen XXII information, and the acquired information, determining whether the subject has a collagen XXII-associated disease or disorder or a pre-disposition to a collagen XXII-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Example 1

Identification and Characterization of Human Collagen XXII cDNA

The human collagen XXII sequence is shown in FIG. 1; SEQ ID NO:1. The nucleic acid sequence includes an initiation codon (ATG) that is double underlined. The region between and inclusive of the initiation codon and the termination codon is a methionine-initiated coding sequence of about 4881 nucleotides, including the termination codon. The coding sequence encodes a 1626 amino acid protein (SEQ ID NO:2), which is shown as SEQ ID NO:2 (FIG. 2).

Two splice variants of collagen XXII have been identified. One variant lacks the nucleotides from nucleotide 3458–3518 of SEQ ID NO:1, and the corresponding protein thereby lacks amino acid residues from amino acid 1005–1024 of SEQ ID NO:2. The collagen XXII protein migrates as a 160 kD polypeptide on SDS PAGE.

Example 2

Anti-Collagen XXII Antibody R34

The 5' non-triple helical domain was expressed in 293 cells and was purified using an incorporated His tag. The recombinant domain was injected into a rabbit to produce antibodies. The rabbit serum was affinity purified on the recombinant fragment and the antibody product is referred to as R34. R34 recognizes the recombinant fragment from XXII but not a similar product from a related collagen, XXIV. R34 does not recognize the His tag. R34 recognizes a band of the appropriate mobility on SDS-PAGE of an extract of muscle Full-length recombinant collagen XXII was made in 293 cells and show the expected electrophoretic mobility after disulfide bond reduction (above). Without reduction, the product shows mobilities of dimers and trimers, as expected for a product that associates into a trimeric triple helix. The recombinant molecule is collagenase sensitive as expected.

Example 3

Tissue Distribution of Collagen XXII by Immunofluorescence Analysis

Immunofluorescent localization of collagen XXII shows deposition in the following locations: myotendinous junctions; in joints, e.g., immediately beneath the articular cartilage of joints; in the basement membrane, e.g., of the outer root sheath at the base of the hair follicles; in the cillary body of the eye, e.g., where the muscle of the lens intersects the zonular fibers; in the heart, e.g., where the heart muscles intersect the cartilage ring in the region of the valves.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a nucleotide sequence that is at least 80% identical to the nucleotide sequence of SEQ ID NO:3.

2. The nucleic acid of claim 1, wherein the nucleotide sequence is at least 85% identical to the nucleotide sequence of SEQ ID NO:3.

3. The nucleic acid of claim 1, wherein the nucleotide sequence is at least 90% identical to the nucleotide sequence of SEQ ID NO:3.

4. The nucleic acid of claim 1, wherein the nucleotide sequence is at least 95% identical to the nucleotide sequence of SEQ ID NO:3.

5. The nucleic acid of claim 1, wherein the nucleotide sequence is at least 98% identical to the nucleotide sequence of SEQ ID NO:3.

6. The nucleic acid of claim 1, wherein the nucleotide sequence is identical to the nucleotide sequence of SEQ ID NO:3.

7. A nucleic acid comprising a nucleotide sequence at least 85% identical to an alternatively spliced variant of SEQ ID NO:1 or SEQ ID NO:3, which variant lacks the sequence corresponding to nucleotides 3458–3518 of SEQ ID NO:1.

8. An isolated nucleic acid consisting of the sequence of SEQ ID NO:1 or SEQ ID NO:3 and its complement.

9. An isolated nucleic acid that encodes a polypeptide having an amino acid sequence which is at least 80% identical to the amino acid sequence of SEQ ID NO:2.

10. The nucleic acid of claim 9, wherein the polypeptide has an amino acid sequence at least 85% identical to the amino acid sequence of SEQ ID NO:2.

11. The nucleic acid of claim 9, wherein the polypeptide has an amino acid sequence at least 90% identical to the amino acid sequence of SEQ ID NO:2.

12. The nucleic acid of claim 9, wherein the polypeptide has an amino acid sequence at least 95% identical to the amino acid sequence of SEQ ID NO:2.

13. The nucleic acid of claim 9, wherein the polypeptide has an amino acid sequence-identical to the amino acid sequence of SEQ ID NO:2.

14. The nucleic acid of claim 9, wherein the polypeptide has one or more of the following activities:
   (a) has the ability to form a triple helix;
   (b) has the ability to form collagen fibrils or fibers;
   (c) localizes to muscle-connective tissue boundaries;
   (d) binds specifically to an antibody that binds to a polypeptide consisting of residues 28–1626 of SEQ ID NO:2; and
   (e) is collagenase sensitive.

15. An isolated nucleic acid that encodes a polypeptide comprising one or more of: residues 1–27 of SEQ ID NO:2; residues 28–1478 of SEQ ID NO:2; residues 1479–1603 of SEQ ID NO:2; and residues 1604–1626 of SEQ ID NO:2.

16. An isolated nucleic acid comprising a nucleotide sequence more than 500 nucleotides in length that hybridizes under highly stringent conditions, comprising 6×SSC at 45° C., followed by one wash in 0.2×SSC, 0.1% SDS at 65° C., to a nucleotide sequence consisting of SEQ ID NO:1 or 3, or the complement of SEQ ID NO:1 or 3, wherein the nucleic acid encodes a polypeptide comprising one or more of the following activities:
   (a) has the ability to form a triple helix;
   (b) has the ability to form collagen fibrils or fibers;
   (c) localizes to muscle-connective tissue boundaries;
   (d) binds specifically to an antibody that binds to a polypeptide consisting of residues 28–1626 of SEQ ID NO: 2; and
   (e) is collagenase sensitive.

17. An isolated nucleic acid comprising a nucleotide sequence more than 500 nucleotides in length that hybridizes under highly stringent conditions, comprising 6×SSC at 45° C., followed by one wash in 0.2×SSC, 0.1% SDS at 65° C., to a nucleotide sequence that encodes a polypeptide having the amino acid sequence of SEQ ID NO:2, or its complement.

18. The nucleic acid of claim 17, wherein the nucleic acid encodes a polypeptide comprising one or more of the following activities:
(a) has the ability to form a triple helix;
(b) has the ability to form collagen fibrils or fibers;
(c) localizes to muscle-connective tissue boundaries;
(d) binds specifically to an antibody that binds to a polypeptide consisting of residues 28–1626 of SEQ ID NO:2; and
(e) is collagenase sensitive.

19. The nucleic acid molecule of any one of claims 1, 6, 9, 13 or 16 further comprising a nucleic acid sequence encoding an amino acid sequence that is heterologous to SEQ ID NO:2.

20. A vector comprising the nucleic acid molecule of any one of claims 1, 6, 9, 13, or 16.

21. An isolated host cell harboring the vector of claim 20.

22. The host cell of claim 21, wherein the host cell is a mammalian cell.

23. The nucleic acid of claim 16 or 17, wherein the nucleic acid is at least 95% identical to SEQ ID NO:3.

24. An isolated probe or primer that hybridizes under highly stringent conditions, comprising 6×SSC at 45° C., followed by one wash in 0.2×SSC, 0.1% SDS at 65° C., to the sense or antisense nucleic acid sequence of SEQ ID NO:1 or SEQ ID NO:3, wherein the isolated probe or primer is between 50 and 300 nucleotides in length.

25. A method for detecting the presence of a nucleic acid molecule in a sample, the method comprising the steps of:

a) contacting the sample with the probe of claim 24; and
b) determining whether the probe binds to a nucleic acid molecule in the sample.

26. The method of claim 25, wherein the sample comprises mRNA molecules.

27. An isolated nucleic acid that comprises a nucleic acid sequence that encodes a polypeptide comprising an amino acid sequence at least 95% identical to a sequence selected from the group consisting of:
(i) residues 1–1004 of SEQ ID NO:2;
(ii) residues 28–1478 of SEQ ID NO:2;
(iii) residues 1479–1603 of SEQ ID NO:2;
(iv) residues 1025–1626 of SEQ ID NO:2; and
(v) SEQ ID NO:2 that lacks amino acids 1005–1024.

28. The nucleic acid of claim 27 wherein the polypeptide comprises an amino acid sequence at least 95% identical to (iv) 1025–1626 of SEQ ID NO:2.

29. The nucleic acid of claim 28 wherein the polypeptide comprises residues 1025–1626 of SEQ ID NO:2.

30. The nucleic acid of claim 27 wherein the polypeptide comprises an amino acid sequence at least 95% identical to (ii) residues 28–1478 of SEQ ID NO:2.

31. The nucleic acid of claim 30 wherein the polypeptide comprises residues 28–1478 of SEQ ID NO:2.

32. The nucleic acid of claim 27 wherein the polypeptide further comprises a glutathione-S-transferase (GST) moiety.

* * * * *